(12) United States Patent
Bui et al.

(10) Patent No.: US 8,936,914 B2
(45) Date of Patent: Jan. 20, 2015

(54) METHODS OF RENAL CELL CARCINOMA PROGNOSIS AND TREATMENT SELECTION WITH CARBONIC ANHYDRASE IX

(75) Inventors: Matthew H. T. Bui, Los Angeles, CA (US); David Seligson, Los Angeles, CA (US); Arie S. Belldegrun, Los Anglels, CA (US)

(73) Assignee: The Regents of the University of California, Oakland, CA (US)

( * ) Notice: Subject to any disclaimer, the term of this patent is extended or adjusted under 35 U.S.C. 154(b) by 1714 days.

(21) Appl. No.: 10/511,465

(22) PCT Filed: Apr. 15, 2003

(86) PCT No.: PCT/US03/11561
§ 371 (c)(1),
(2), (4) Date: Feb. 7, 2005

(87) PCT Pub. No.: WO03/089659
PCT Pub. Date: Oct. 30, 2003

(65) Prior Publication Data
US 2005/0158809 A1   Jul. 21, 2005

Related U.S. Application Data

(60) Provisional application No. 60/373,193, filed on Apr. 16, 2002, provisional application No. 60/384,460, filed on May 31, 2002.

(51) Int. Cl.
| | | |
|---|---|---|
| *C12Q 1/00* | (2006.01) | |
| *G01N 33/53* | (2006.01) | |
| *G01N 33/567* | (2006.01) | |
| *G01N 33/574* | (2006.01) | |
| *G01N 1/00* | (2006.01) | |
| *G01N 33/48* | (2006.01) | |
| *G01N 33/566* | (2006.01) | |
| *G01N 33/573* | (2006.01) | |

(52) U.S. Cl.
CPC ........ *G01N 33/57438* (2013.01); *G01N 33/573* (2013.01); *G01N 2333/988* (2013.01)
USPC .............. 435/7.1; 435/4; 435/6.14; 435/7.21; 435/7.23; 436/63; 436/64; 436/174; 436/501

(58) Field of Classification Search
CPC ......... A61K 6/00; A61K 38/00; A61K 38/16; A61K 38/17; A61K 38/19; A61K 38/20; A61K 38/2013; G01N 1/00; G01N 33/00; G01N 33/48; G01N 33/483; G01N 33/4833; G01N 33/53; G01N 33/574; G01N 33/57407; G01N 33/57438
USPC ........ 435/4, 6.14, 7.1, 7.21, 7.23; 436/63, 64, 436/174, 501
See application file for complete search history.

(56) References Cited

U.S. PATENT DOCUMENTS

| | | |
|---|---|---|
| 3,766,162 A | 10/1973 | Spector |
| 3,791,932 A | 2/1974 | Schuurs et al. |
| 3,817,837 A | 6/1974 | Rubenstein et al. |
| 4,233,402 A | 11/1980 | Maggio et al. |
| 5,387,676 A | 2/1995 | Zavada et al. |
| 5,955,075 A | 9/1999 | Zavada et al. |
| 5,972,353 A | 10/1999 | Zavada et al. |
| 5,981,711 A | 11/1999 | Zavada et al. |
| 5,989,838 A | 11/1999 | Zavada et al. |
| 6,004,535 A | 12/1999 | Zavada et al. |
| 6,027,887 A | 2/2000 | Zavada et al. |
| 6,051,226 A | 4/2000 | Zavada et al. |
| 6,069,242 A | 5/2000 | Zavada et al. |
| 6,093,548 A | 7/2000 | Zavada et al. |
| 6,204,370 B1 | 3/2001 | Zavada et al. |
| 6,297,041 B1 | 10/2001 | Zavada et al. |
| 6,297,051 B1 | 10/2001 | Zavada et al. |
| 6,770,438 B2 | 8/2004 | Zavada et al. |
| 6,774,117 B1 | 8/2004 | Zavada et al. |
| 2002/0058041 A1* | 5/2002 | Belldegrun et al. ........ 424/185.1 |
| 2002/0137910 A1 | 9/2002 | Zavada et al. |
| 2003/0049828 A1 | 3/2003 | Zavada et al. |
| 2004/0259126 A1 | 12/2004 | Zavada et al. |
| 2005/0003425 A1 | 1/2005 | Zavada et al. |
| 2005/0031623 A1 | 2/2005 | Pastorek et al. |

FOREIGN PATENT DOCUMENTS

| | | |
|---|---|---|
| WO | WO 93/18152 A1 | 9/1993 |
| WO | WO 95/34650 | * 12/1995 |
| WO | WO 95/34650 | * 12/1998 |

OTHER PUBLICATIONS

Ivanov et al. Expression of hypoxia-inducible cell-surface transmembrane carbonic anhydrases in human cancer. American Journal of Pathology 158(3): 905-919, Mar. 2001.*
GenCore amino acid databases. Sequence 2 of U.S. Patent 5,995,075 issued Sep. 21, 1999.*
Cangiano et al. Journal of Clinical Oncology 17(2): 523-528, Feb. 1999.*
Bretheau et al. (1995) "Prognostic value of nuclear grade of renal cell carcinoma." *Cancer* (Phila.) 76(12): 2543-2549.
Brewer et al. (1996) "A study of biomarkers in cervical carcinoma and clinical correlation of the novel biomarker MN," *Gynecologic Oncology* 63: 337-344. (Article No. 0333).

(Continued)

*Primary Examiner* — Alana Harris Dent
(74) *Attorney, Agent, or Firm* — Kilpatrick Townsend & Stockton LLP

(57) ABSTRACT

The present invention provides methods of aiding in a renal cell carcinoma prognosis that include quantifying expressed carbonic anhydrase in samples derived from renal cell carcinoma patients. The methods also identify patients that are likely to respond positively to selected courses of treatment. The invention further provides related computer program products.

5 Claims, 5 Drawing Sheets

(56) References Cited

OTHER PUBLICATIONS

Bui et al. (2001) "Prognostic factors and molecular markers for renal cell carcinoma." *Expert Review of Anticancer Therapy*, 1(4): 565-575.
Bui et al. (2003) "Carbonic Anhydrase IX Is an Independent Predictor of Survival in Advanced Renal Clear Cell Carcinoma: Implications for Prognosis and Therapy." *Clinical Cancer Research*, 9:802-811.
Dalbadie-McFarland et al. (1982) "Oligonucleotide-Directed Mutagenesis as a General and Powerful Method for Studies of Protein Function" *Proceeding of the National Academy of Sciences USA*, 79: 6409-6413.
Der and Stanbridge (1981) "A tumor-specific membrane phosphoprotein marker in human cell hybrids." *Cell* 26: 429-438.
Divgi et al. (1998) "Phase I/II radioimmunotherapy trial with iodine-131-labeled monoclonal antibody G250 in metastatic renal cell carcinoma," *Clinical Cancer Research*, 4: 2729-2739.
Elson et al. (1988) "Prognostic factors for survival in patients with recurrent or metastatic renal cell carcinoma." *Cancer Research*, 48: 7310-7313.
Figlin (1999) "Renal cell carcinoma: management of advanced disease." *The Journal of Urology*, 161:381-386.
Flanigan et al. (2001) "Nephrectomy followed by interferon α-2b compared with interferon α-2b alone for metastatic renal-cell cancer." *New England Journal of Medicine*, 345(23): 1655-1659.
Fuhrman et al. (1982) "Prognostic significance of morphologic parameters in renal cell carcinoma." *The American Journal of Surgical Pathology*, 6(7): 655-663.
Galfre and Milstein (1981) "Preparation of Monoclonal Antibodies: Strategies and Procedures." *Methods in Enzymology*, 73:1-46.
Giatromanolaki et al. (2001) "Expression of hypoxiainducible carbonic anhydrase-9 relates to angiogenic pathways and independently to poor outcome in non-small cell lung cancer." *Cancer Research*, 61:7992-7998.
Glennie and Stevenson (1982) "Univalent antibodies kill tumour cells in vitro and in vivo." *Nature* 295: 712-714.
Gorman et al. (1991) "Reshaping a Therapeutic CD4 Antibody." *Proceeding of the National Academy of Sciences USA*, 88:4181-4185.
Ivanov et al. (1998) "Down-regulation of transmembrane carbonic anhydrases in renal cell carcinoma cell lines by wild-type von Hippel-Lindau transgenes," *Proceeding of the National Academy of Sciences USA*, 95:12596-12601.
Ivanov et al. (2001) "Expression of hypoxia-inducible cell-surface transmembrane carbonic anhydrases in human cancer." *Amreican Journal of Pathology*, 158(3):905-919.
Jemal et al. (2002) "Cancer Statittics, 2002" *CA-Cancer J. Clin.*, 52(1):23-47.
Kaplan and Meier (1958) "Nonparametric estimation from incomplete observations." *Amreican Statistical Association Journal*, 53: 457-481.
Kononen et al. (1998) "Tissue microarrays for high-throughput molecular profiling of tumor specimens." *Nature Medicine*, 4(7): 844-847.
Liao et al. (1994) "Identification of the MN antigen as a diagnostic biomarker of cervical intraepithelial squamous and glandular neoplasia and cervical carcinomas." *Amreican Journal of Pathology*, 145(3): 598-609.
Liao et al. (1997) "Identification of the MN/CA9 protein as a reliable diagnostic biomarker of clear cell carcinoma of the kidney." *Cancer Research*, 57: 2827-2831.
Loncaster et al. (2001) "Carbonic anhydrase (CA IX) expression, a potential new intrinsic marker of hypoxia: correlations with tumor oxygen measurements and prognosis in locally advanced carcinoma of the cervix." *Cancer Research*, 61:6394-6399.
Kohler and Milstein (1975) "Continuous cultures of fused cells secreting antibody of predefined specificity." *Nature* 256: 495-497.
Motzer et al. (1999) "Survival and prognostic stratification of 670 patients with advances renal cell carcinoma." *Journal of Clinical Oncology*, 17(8): 2530-2540.
Murakami et al. (1999) "MN/CA9 gene expression as a potential biomarker in renal cell carcinoma." *BJU International*, 83: 743-747.
Olive et al. (2001) "Carbonic anhydrase 9 as an endogenous marker for hypoxic cells in cervical cancer," *Cancer Research*, 61:8924-8929.
Olsson and Kaplan (1980) "Human-Hunam hybridomas producing monoclonal antibodies of predefined antigenic spegificity." *Proceeding of the National Academy of Sciences USA*, 77(9): 5429-5431.
Oosterwijk et al. (1986) "Immunohistochemical analysis of monoclonal antibodies to renal antigens." *American Journal of Pathology* 123(2):301-309.
Oosterwijk et al. (1986) "Monoclonal antibody G250 recognizes a determinant present in renal cell carcinoma and absent from normal kidney." *International Journal of Cancer*, 38: 489-494.
Oosterwijk et al. (1996) "Molecular characterization of the renal cell carcinomaassociated antigen G250," *Proceedings of the National Association for Cancer Research*, 37: #3147.
Pantuck et al. (2001) "The changing natural history of renal cell carcinoma." *The Journal of Urology*, 166:1611-1623.
Parkkila et al. (2000) "Carbonic anhydrase inhibitor suppresses invasion of renal cancer cells in vitro." *Proceeding of the National Academy of Sciences USA*, 97(5):2220-2224.
Pastorek et al. (1994) "Cloning and characterization of MN, a human tumor associated protein with a domain homologous to carbonic anhydrase and a putative helix-loop-helix DNA binding segment." *Oncogene* 9: 2877-2888.
Pastoreková et al. (1992) "A Novel Quasi-viral Agent, MaTu, Is a Two-Component ystem." *Virology* 187 :620-626.
Rak et al. (2002) "What do oncogenic mutations have to do with angiogenesis/vascular dependence of tumors?" *Cancer Research*, 62:1931-1934.
Roila et al. (1991) "Intra and interobserver variability in cancer patients' performance status assessed according to Karnofsky and ECOG scales." *Annals of Oncology* 2: 437-439.
Saarnio et al. (1998) "Immunohistochemical study of colorectal tumors for expression of a novel transmembrane carbonic anhydrase. MN/CA IX, with potential value as a marker of cell proliferation." *Amreican Journal of Pathology*, 153(1):279-285.
Schlom et al. (1980) "Generation of human monoclonal antibodies reactive with human mammary carcinoma cells." *Proceeding of the National Academy of Sciences USA*, 77(11):6841-6845.
Shearman et al. (1991) "Construction, expression, and biologic activity of murine/human chimeric antibodies with specificity for the human alpha/beta T cell receptor." *The Journal of Immunology*, 146(3): 928-935.
Shi et al. (1999) "Constitutive and inducible interleukin 8 expression by hypoxia and acidosis renders human pancreatic cancer cells more tumorigenic and metastatic." *Clinical Cancer Research*, 5:3711-3721.
Slamon et al. (2001) "Use of chemotherapy plus a monoclonal antibody against HER2 for metastatic breast cancer that overexpresses HER2." *The New England Journal of Medicine*, 344(11):783-792.
Sobin and Fleming (1997) "TNM Classification of Malignant Tumors, 5 Ed . . . " *Union Internationale Contre le Cancer and the American Joint Committee on Cancer, Cancer* (Phila.) 80: 1803-1804.
Steffens et al. (1997) "Targeting of renal cell carcinoma with iodine-131-labeled chimeric monoclonal antibody G250," *Journal of Clinical Oncology*, 15(4): 1529-1537.
Steffens et al. (1999) "Immunohistochemical analysis of tumor antigen saturation following injection of monoclonal antibody G250." *Anticancer Research*, 19: 1197-1200.
Steffens et al. (1999) "Phase I radioimmunotherapy of metastatic renal cell carcinoma with 131l-labeled chimeric monoclonal antibody G250." *Clinical Cancer Research*, 5: 3268s-3274s.
Störkel et al. (1997) "Classification of renal cell carcinoma: Workgroup No. 1." *Union Internationale Contra le Cancer (UICC) and the American Joint Committee on Cancer (AJCC) Cancer*, 80(5): 987-989.
Tso et al. (2001) "Induction of G250-targeted and T-cell-mediated antitumor activity against renal cell carcinoma using a chimeric fusion protein consisting of G250 and granulocyte/monocyte-colony stimulating factor." *Cancer Research*, 61:7925-7933.

(56) References Cited

OTHER PUBLICATIONS

Turner et al. (1997) "MN antigen expression in normal, preneoplastic, and neoplastic esophagus: a clinicopathological study of a new cancer-associated biomarker." *Human Pathololgy*, 28: 740-744.

Uemura et al. (1994) "Vaccination with anti-idiotype antibodies mimicking a renal cell carcinoma-associated antigen induces tumor immunity." *International Journal of Cancer*, 58: 555-561.

Uemura et al. (1997) "Expression of tumor-associated antigen MN/G250 in urologic carcinoma: potential therapeutic target." *The Journal of Urology*, 157(4)(Suppl): #1475.

Uemura et al. (1999) "MN/CA IX/G250 as a potential target for immunotherapy of renal cell carcinomas." *British Journal of Cancer*, 81(4):741-746.

Van Dijk et al. (1989) "Induction of tumor-cell lysis by bi-specific monoclonal antibodies recognizing renal-cell carcinoma and CD3 antigen." *International Journal of Cancer*, 43: 344-349.

Vissers et al. (1999) "The renal cell carcinoma associated antigen G250 encodes a human leukocyte antigen (HLA)-A2.1-restricted epitope recognized by cytotoxic T lymphocytes." *Cancer Research*, 59: 5554-5559.

Wykoff et al. (2000) "Hypoxia-inducible expression of tumor-associated carbonic anhydrases." *Cancer Research*, 60:7075-7083.

Wykoff et al. (2000) "Identification of novel hypoxia dependent and independent target genes of the von Hippel-Lindau (VHL) tumour suppressor by mRNA differential expression profiling." *Oncogene*, 19: 6297-6305.

Žavada et al. (1993) "Expression of MaTu-MN protein in human tumor cultures and in clinical specimens." *International Journal of Cancer*, 54: 268-274.

Zisman et al. (2001) "Improved prognostication of renal cell carcinoma using an integrated staging system." *Journal of Clinical Oncology*, 19(6):1649-1657.

* cited by examiner

METHODS OF RENAL CELL CARCINOMA PROGNOSIS AND TREATMENT SELECTION WITH CARBONIC ANHYDRASE IX

CROSS-REFERENCES TO RELATED APPLICATIONS

Pursuant to 35 U.S.C. §119, the present application claims the benefit of and priority to U.S. Provisional Application No. 60/373,193, entitled "CARBONIC ANHYDRASE IX FOR MOLECULAR CLASSIFICATION, DIAGNOSIS, AND PROGNOSTICATION," filed on Apr. 16, 2002 by Bui et al., and to U.S. Provisional Application No. 60/384,460, entitled "CARCINOMA DIAGNOSIS AND PROGNOSTICATION WITH CARBONIC ANHYDRASE IX," filed on May 31, 2002 by Bui et al., the disclosures of which are incorporated by reference in their entirety for all purposes.

COPYRIGHT NOTIFICATION

Pursuant to 37 C.F.R. §1.71(e), Applicants note that a portion of this disclosure contains material which is subject to copyright protection. The copyright owner has no objection to the facsimile reproduction by anyone of the patent document or patent disclosure, as it appears in the Patent and Trademark Office patent file or records, but otherwise reserves all copyright rights whatsoever.

STATEMENT AS TO RIGHTS TO INVENTIONS MADE UNDER FEDERALLY SPONSORED RESEARCH AND DEVELOPMENT

Not Applicable.

BACKGROUND OF THE INVENTION

In recent years, renal cell carcinoma (RCC) has accounted for over 31,000 new cases of cancer and contributed to approximately 12,000 deaths in the United States (Jemal et al. (2002) "Cancer statistics, 2002," *CA—Cancer J. Clin.* 52:23-47). Clear cell carcinoma was the predominant subtype comprising up to 85% of RCCs. One-third of patients diagnosed with kidney cancer have evidence of metastatic disease at the time of diagnosis and up to half of those treated for localized disease eventually relapse (Figlin (1999) "Renal cell carcinoma: management of advanced disease," *J. Urol.* 161:381-386; discussion 386-387). The natural history of RCC is complex and influenced by factors other than stage (Pantuck et al. (2001) "The changing natural history of renal cell carcinoma," *J. Urol.* 166:1611-1623). Patient and tumor-related factors have been proposed as prognostic factors (Bretheau et al. (1995) "Prognostic value of nuclear grade of renal cell carcinoma," *Cancer (Phila.)*, 76:2543-2549, Elson et al. (1988) "Prognostic factors for survival in patients with recurrent or metastatic renal cell carcinoma," *Cancer Res.* 48:7310-7313, Motzer et al. (1999) "Survival and prognostic stratification of 670 patients with advanced renal cell carcinoma," *J. Clin. Oncol.* 17:2530-2540, and Bui et al. (2001) "Prognostic factors and molecular markers for renal cell carcinoma," *Exp. Rev. Anticancer Ther.* 1:565-575). Therefore, understanding how the complex interactions between multiple prognostic factors contribute to the clinical behavior of RCC is important for patient assessment, outcome prediction, and therapy planning.

Carbonic anhydrase IX (CAIX) protein, a member of the carbonic anhydrase family, is thought to play a role in the regulation of cell proliferation in response to hypoxic conditions and may be involved in oncogenesis and tumor progression (Pastorek et al. (1994) "Cloning and characterization of MN, a human tumor-associated protein with a domain homologous to carbonic anhydrase and a putative helix-loop-helix DNA binding segment," *Oncogene* 9:2877-2888, Wykoff et al. (2000) "Identification of novel hypoxia dependent and independent target genes of the von Hippel-Lindau (VHL) tumour suppressor by mRNA differential expression profiling," *Oncogene* 19:6297-6305, and Ivanov et al. (2001) "Expression of hypoxia-inducible cell-surface transmembrane carbonic anhydrases in human cancer," *Am. J. Pathol.* 158:905-919). Previous studies using a monoclonal antibody against CAIX have shown that CAIX is induced constitutively in certain tumor types but is absent in most normal tissues with the exception of epithelial cells of the gastric mucosa (Ivanov et al. (2001) *Am. J. Pathol.* 158:905-919 (above), Zavada et al. (1993) "Expression of MaTu-MN protein in human tumor cultures and in clinical specimens," *Int. J. Cancer* 54:268-274, Oosterwijk et al. (1986) "Monoclonal antibody G250 recognizes a determinant present in renal cell carcinoma and absent from normal kidney," *Int. J. Cancer* 38:489-494, and Murakami et al. (1999) "MN/CA9 gene expression as a potential biomarker in renal cell carcinoma," *BJU Int.* 83:743-747). Furthermore, previous immunobiochemical studies of malignant and benign renal tissues revealed that CAIX was also highly expressed in RCC, suggesting that CAIX expression may be a useful diagnostic biomarker (Uemura et al. (1999) "MN/CA IX/G250 as a potential target for immunotherapy of renal cell carcinomas," *Br. J. Cancer* 81:741-746 and Liao et al. (1997) "Identification of the MN/CA9 protein as a reliable diagnostic biomarker of clear cell carcinoma of the kidney," *Cancer Res.*, 57:2827-2831). Clinical tumor targeting studies by inter venous injection with a monoclonal antibody to CAIX have shown localization to RCC tumors in a mouse tumor model (Steffens et al. (1999) "Immunohistochemical analysis of tumor antigen saturation following injection of monoclonal antibody G250," *Anticancer Res.* 1197-1200) and have been applied in clinical trials to treat metastatic RCC (Steffens et al. (1997) "Targeting of renal cell carcinoma with iodine-131-labeled chimeric monoclonal antibody G250," *J. Clin. Oncol.* 15:1529-1537, Divgi et al. (1998) "Phase I/II radioimmunotherapy trial with iodine-131-labeled monoclonal antibody G250 in metastatic renal cell carcinoma," *Clin. Cancer Res.* 4:2729-2739, and Steffens et al. (1999) "Phase I radioimmunotherapy of metastatic renal cell carcinoma with 131I-labeled chimeric monoclonal antibody G250," *Clin. Cancer Res.* 3268s-3274s). However, prior to the present invention the relationship between CAIX expression and RCC survivorship was unknown.

Traditionally, stage, grade, and performance status have been the most useful predictors of outcome for RCC (Zisman et al. (2001) "Improved prognostication of renal cell carcinoma using an integrated staging system," *J. Clin. Oncol.* 19:1649-1657). However, molecular markers can make a significant impact on the diagnosis and treatment of RCC. Tumor markers provide not only prognostic information to aid in the identification of patients at risk for recurrence or metastasis but can also facilitate the rational use of targeted therapeutic interventions as well. This concept has been demonstrated for the molecular marker, Her2/neu, and its use in the prognosis and treatment of breast cancer (Slamon et al. (2001) "Use of chemotherapy plus a monoclonal antibody against HER2 for metastatic breast cancer that overexpresses HER2," *N. Engl. J. Med.* 344:783-792). Furthermore, the recent development of microarray technologies and other analytical techniques are permitting the rapid identification and validation of diagnostic and molecular markers.

Previous immunohistochemical investigations (Liao et al. (1994) "Identification of the MN antigen as a diagnostic biomarker of cervical intraepithelial squamous and glandular neoplasia and cervical carcinomas," *Am. J. Pathol.* 145:598-609) have suggested that CAIX is a potential diagnostic biomarker for cervical neoplasms. An immunohistochemical study of RCC (Liao et al. (1997) *Cancer Res.* 57:2827-2831 (above)) also reported that CAIX was expressed in all examined RCCs, including granular, spindle, and papillary carcinomas, but not in those consisting of chromophobe histology or in benign renal lesions, including oncocytomas. Yet another study of 187 RCC reported CAIX expression in 87% of tumors by immunohistochemistry (Uemura et al. (1999) "MN/CA IX/G250 as a potential target for immunotherapy of renal cell carcinomas," *Br. J. Cancer* 81:741-746). In a study of 321 primary clear cell RCC tumors, the inventors confirmed the high specificity of CAIX staining with 94% positive staining in clear cell carcinomas in the kidney. Other studies have reported that CAIX detection by reverse transcription-PCR assays in tumor specimens have a high correlation with immunohistochemistry (Uemura et al. (1999) *Br. J. Cancer* 81:741-746 (above) and Murakami et al. (1999) "MN/CA9 gene expression as a potential biomarker in renal cell carcinoma," *BJU Int.* 83:743-747).

Targeted therapies directed at CAIX are being developed to exploit the exclusivity of CAIX expression in RCC for the treatment of metastatic disease. For example, early Phase I and II clinical trials have been addressing the feasibility of radioimmunotherapy using a monoclonal antibody against CAIX coupled to a radioisotope and have shown only minor therapeutic responses for patients with metastatic RCC (Steffens et al. (1999) *Anticancer Res.* 1197-1200 (above), Steffens et al. (1997) 15:1529-1537 (above), Divgi et al. (1998) *Clin. Cancer Res.* 4:2729-2739 (above), and Steffens et al. (1999) *Clin. Cancer Res.* 3268s-3274s (above)). Other therapy modalities target the immunogenicity of CAIX as a RCC tumor antigen (Vissers et al. (1999) "The renal cell carcinoma associated antigen G250 encodes a human leukocyte antigen (HLA)-A2.1-restricted epitope recognized by cytotoxic T lymphocytes," *Cancer Res.* 59:5554-5559) by developing tumor-cell vaccines and dendritic cell vaccines (Uemura et al. (1994) "Vaccination with anti-idiotype antibodies mimicking a renal cell carcinoma-associated antigen induces tumor immunity," *Int. J. Cancer* 58:555-561 and Tso et al. (2001) "Induction of G250-targeted and T-cell-mediated antitumor activity against renal cell carcinoma using a chimeric fusion protein consisting of G250 and granulocyte/monocyte-colony stimulating factor," *Cancer Res.* 61:7925-7933). Yet another targeted approach would be to inhibit CAIX activity with chemical inhibitors. A recent study reported that a carbonic anhydrase inhibitor, acetazolamide, was able to inhibit the invasive capacity of renal cancer cells in vitro (Parkkila et al. (2000) "Carbonic anhydrase inhibitor suppresses invasion of renal cancer cells in vitro," *Proc. Natl. Acad. Sci. USA* 97:2220-2224). Because CAIX is a cell surface protein unlike intracellular carbonic anhydrase isoenzymes, the design of specific chemical inhibitors of CAIX that are cell impermeable may demonstrate higher selectivity and less toxicity for suppressing renal cancer invasion.

The molecular role of CAIX in tumorigenesis is currently being elucidated, and RCC provides a unique model to study the role of hypoxia in solid tumor oncogenesis and progression. Constitutive expression of CAIX as a result of von Hippel-Lindau protein mutations (Ivanov et al. (1998) "Down-regulation of transmembrane carbonic anhydrases in renal cell carcinoma cell lines by wild-type von Hippel-Lindau transgenes," *Proc. Natl. Acad. Sci. USA* 95:12596-12601) has been described for RCC. However, recent studies now indicate that expression of CAIX is regulated by the hypoxia-inducible factor 1 transcriptional complex that mediates expression of a number of genes in response to hypoxic conditions (Wykoff et al. (2000) "Hypoxia-inducible expression of tumor-associated carbonic anhydrases," *Cancer Res.* 60:7075-7083). Furthermore, higher CAIX expression has been reported in perinecrotic regions of several tumor types (Ivanov et al. (2001) *Am. J. Pathol.* 158:905-919 (above) and Olive et al. (2001) "Carbonic anhydrase 9 as an endogenous marker for hypoxic cells in cervical cancer," *Cancer Res.* 61:8924-8929). It has been postulated that cell surface carbonic anhydrases regulate acid-base balance to optimize conditions in the tumor invasiveness (Ivanov et al. (2001) *Am. J. Pathol.* 158:905-919 (above)). Acidification of the extracellular matrix is known to induce expression of angiogenic factors (Shi et al. (1999) "Constitutive and inducible interleukin 8 expression by hypoxia and acidosis renders human pancreatic cancer cells more tumorigenic and metastatic," *Clin. Cancer Res.* 5:3711-3721) and may inhibit cellular immunity (Giatromanolaki et al. (2001) "Expression of hypoxiainducible carbonic anhydrase-9 relates to angiogenic pathways and independently to poor outcome in non-small cell lung cancer," *Cancer Res.* 61:7992-7998), which additionally promotes tumor aggressiveness. In addition, there is some evidence for the association of CAIX with loss of contact inhibition and anchorage dependence of cancer cells (Parkkila et al. (2000) *Proc. Natl. Acad. Sci. USA* 97:2220-2224 (above)).

From the foregoing, it is apparent that methods of correlating CAIX expression with RCC survivorship are desirable. More specifically, it is desirable to predict clinical outcome and/or to identify high-risk patients in need of adjuvant immunotherapy, CAIX-targeted therapies, or other methods of treatment based, at least in part, on CAIX expression levels. These and a variety of additional features of the present invention will become evident upon complete review of the following disclosure.

SUMMARY OF THE INVENTION

The present invention generally relates to the science of oncology. More specifically, the invention provides methods that yield prognostic information for patients afflicted with renal cell carcinoma (RCC), particularly, renal clear cell carcinoma. The methods described herein include quantifying carbonic anhydrase IX (CAIX), which is a molecular marker for kidney cancer. In addition to reliably predicting clinical outcome, the methods of the present invention also identify high-risk patients in need of adjuvant immunotherapy and/or CAIX-targeted therapies, among other courses of treatment. The methods of the invention are optionally performed, at least in part, in a computer or other information appliance, and accordingly, the invention further provides computer program products.

More specifically, immunohistochemical analysis using a CAIX monoclonal antibody was performed on tissue microarrays constructed from paraffin-embedded specimens from patients (N=321) treated by nephrectomy for clear cell RCC. CAIX staining was correlated with response to treatment, clinical factors, pathologic features and survival. Median follow-up was 45 months (0.3-117) and disease-specific survival (DSS) was the primary end point assessed. All statistical tests were two-sided.

CAIX staining was present in 94% of clear cell RCCs. Survival tree analysis determined that a cut-off of 85% CA IX staining provided the most accurate prediction of survival. Low CAIX (≤85%) staining was an independent poor prognostic factor for survival for patients with metastatic RCC, with a hazard ratio of 3.10 (P<0.001). CAIX significantly sub-stratified patients with metastatic disease when analyzed by T stage, Fuhrman grade, nodal involvement and ECOG performance status (P<0.001, <0.001, <0.001, <0.001, respectively). For patients with nonmetastatic RCC and at high risk for progression, low CAIX predicted a worse outcome similar to patients with metastatic disease (P=0.058). Overall expression of CAIX decreased with development of metastasis; as demonstrated by the lower CAIX staining levels in metastatic lesions relative to matched primary tumor specimens (P=0.036). All complete responders to interleukin-2 (IL-2) immunotherapy (8%) included patients with high CAIX (>85%) staining.

Based on the data described herein, CAIX is the most significant molecular marker described in kidney cancer to date. Decreased CAIX levels are independently associated with poor survival in advanced RCC. CAIX reflects significant changes in tumor biology that can be used to predict clinical outcome and identify high-risk patients in need of, e.g., adjuvant immunotherapy and CAIX-targeted therapies.

Accordingly, in one aspect, the invention relates to a method of aiding in a renal cell carcinoma prognosis that includes (a) quantifying expressed carbonic anhydrase IX (CAIX), if any, present in one or more samples derived from a subject diagnosed with renal cell carcinoma (e.g., renal clear cell carcinoma) to produce quantified CAIX expression data. The method also includes (b) correlating the quantified CAIX expression data with a probability of a renal cell carcinoma prognosis for the subject. The expressed CAIX typically includes a CAIX polypeptide, a fragment of a CAIX polypeptide, an mRNA that encodes a CAIX polypeptide, or the like. Although other quantification techniques are optionally utilized, in preferred embodiments, the expressed CAIX is quantified by immunohistochemical staining. In addition, the samples are generally derived from a renal tumor and/or a metastatic lesion derived from a renal tumor.

Quantified CAIX expression data correlates with various outcomes for RCC patients. For example, when the quantified CAIX expression data comprises a quantification percentage of more than 85% that quantification percentage correlates with a better prognosis for the subject than a quantification percentage of 85% or less when the subject is diagnosed with metastatic renal cell carcinoma. Further, when the quantified CAIX expression data comprises a quantification percentage of 85% or less that quantification percentage correlates with a better prognosis for the subject than a quantification percentage of 85% or less when the subject is diagnosed with non-metastatic renal cell carcinoma of T stage≥3 and Fuhrman grade≥2.

The method additionally identifies RCC patients that may benefit from particular courses of treatment. To illustrate, when the quantified CAIX expression data comprises a quantification percentage of more than 85% that quantification percentage further correlates with a likely positive response to, e.g., interleukin-2 (IL-2) immunotherapy, or one or more CAIX-targeted therapies, for the subject. In addition, when the quantified CAIX expression data comprises a quantification percentage of 85% or less that quantification percentage further correlates with a likely positive response to an adjuvant immunotherapy for the subject when the subject is diagnosed with non-metastatic renal cell carcinoma of T stage≥3 and Fuhrman grade≥2.

In another aspect, the invention relates to a method of aiding in a renal clear cell carcinoma prognosis that includes (a) quantifying expressed CAIX polypeptides, if any, present in one or more samples derived from a subject diagnosed with renal clear cell carcinoma to produce quantified CAIX polypeptide expression data in which the samples are derived from a renal tumor and/or a metastatic lesion derived from a renal tumor. The method also includes (b) correlating the quantified CAIX polypeptide expression data with a probability of a renal clear cell carcinoma prognosis in which a quantification percentage of 85% stratifies the prognosis for the subject. In preferred embodiments, the expressed CAIX polypeptides are quantified by immunohistochemical staining and the quantification percentage comprises a positive staining percentage.

The quantified CAIX expression data produced with this method also correlates with various outcomes for RCC patients and further identifies RCC patients that may need specific courses of treatment. For example, a quantification percentage of more than 85% correlates with a better prognosis for the subject than a quantification percentage of 85% or less when the subject is diagnosed with metastatic renal clear cell carcinoma, or when the subject is diagnosed with non-metastatic renal clear cell carcinoma of T stage≥3 and Fuhrman grade≥2. A quantification percentage of more than 85% for a sample derived from the renal tumor correlates with a lower probability of metastasis than a quantification percentage of 85% or less for the sample derived from the renal tumor. In addition, a quantification percentage of more than 85% further correlates with a likely positive response to interleukin-2 immunotherapy for the subject, or with a likely positive response to one or more CAIX-targeted therapies for the subject. Moreover, a quantification percentage of 85% or less further correlates with a likely positive response to an adjuvant immunotherapy for the subject when the subject is diagnosed with non-metastatic renal cell carcinoma of T stage≥3 and Fuhrman grade≥2.

In certain embodiments of the methods described herein, the quantified CAIX expression data are in a computer-readable form. In these embodiments, (b) typically comprises operating a programmable computer that comprises at least one database and executing an algorithm that determines closeness-of-fit between the computer-readable quantified CAIX expression data and database entries, which entries correspond to clinical and/or pathological data for a population of renal carcinoma patients (e.g., renal clear cell carcinoma patients) to thereby correlate the quantified CAIX expression data with the probability of the renal carcinoma prognosis (e.g., renal clear cell carcinoma prognosis) for the subject.

In yet another aspect, the present invention provides a computer program product comprising a computer readable medium having one or more logic instructions. The computer readable medium includes logic instructions for (a) receiving quantified CAIX expression data derived from a subject diagnosed with renal cell carcinoma. The computer readable medium also includes logic instructions for (b) determining closeness-of-fit between the quantified CAIX expression data and database entries, which entries correspond to clinical and/or pathological data for a population of renal cell carcinoma patients to thereby correlate the quantified CAIX expression data with a probability of a renal cell carcinoma prognosis for the subject.

BRIEF DESCRIPTION OF THE DRAWINGS

FIG. 1A shows the pattern of CAIX staining in the tissue cores (at ×100 and ×400 magnification). Normal kidney tissues (panels A1-A2) were ubiquitously negative for CAIX. Clear cell RCC had intense membrane staining for high levels (>85% positive staining, panels A3-A4) or low levels (≤85%, panels A5-A6) of CAIX. FIG. 1B is a data graph (abscissa—percentage of CAIX staining in each specimen; ordinate—fraction of all tumor specimens, N=321) that shows distribution of CAIX staining for all tumor specimens. FIG. 1C is a data graph (abscissa—months following nephrectomy; ordinate—disease-specific survival (DSS)) that shows the Kaplan-Meier curves of DSS for patients according to CAIX expression and metastatic status.

FIG. 5 is a bar graph showing the percentage of CAIX staining at the maximal intensity in the primary tumor and corresponding metastatic lesion in 15 patients (P=0.036).

DETAILED DISCUSSION OF THE INVENTION

I. Definitions

Figure 1:
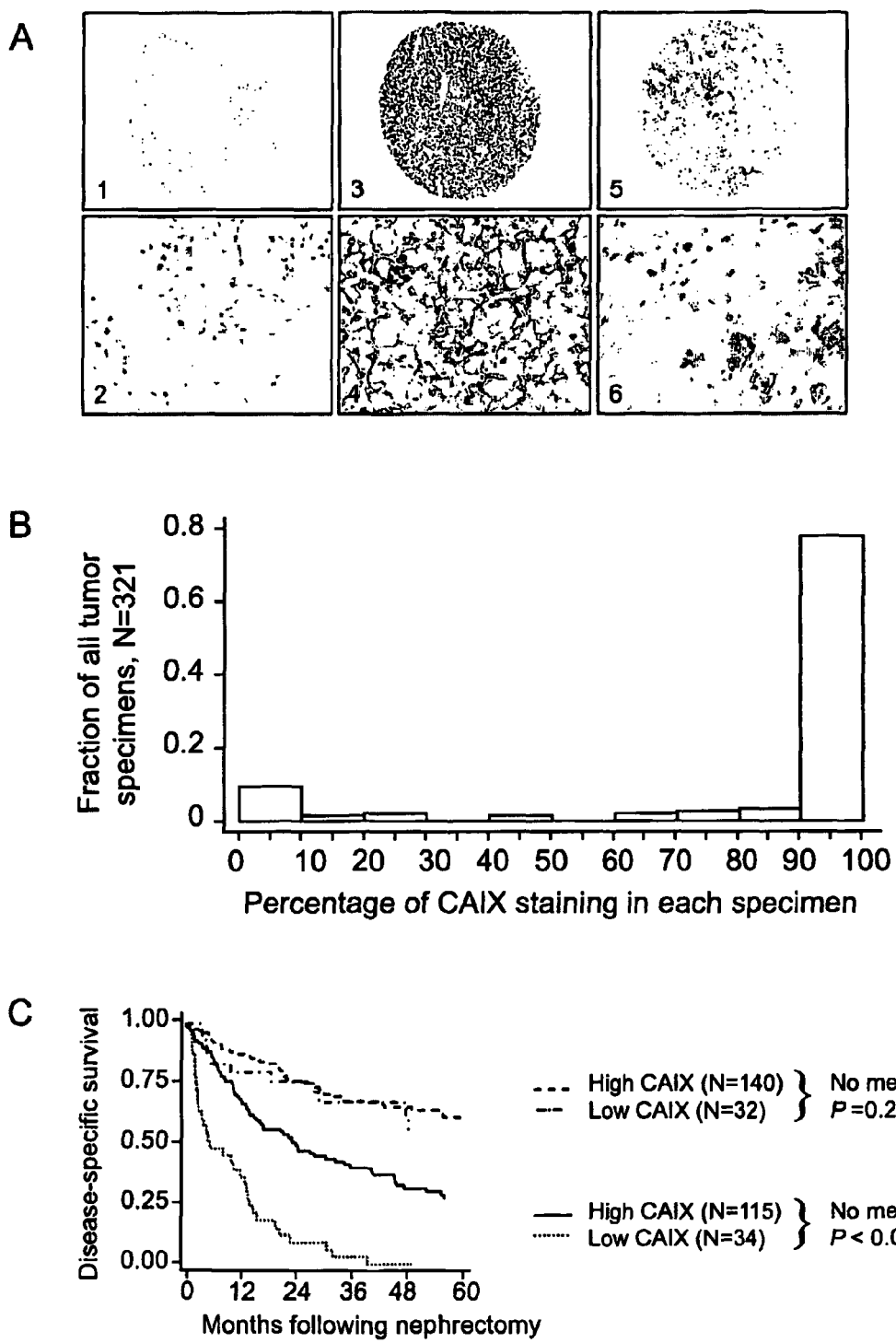
FIGS. 1A-C show an immunohistochemical analysis of CAIX and DSS according to the levels of CAIX expression for patients with clear RCC. In particular.

Before describing the present invention in detail, it is to be understood that this invention is not limited to particular methods or computer program products, which can, of course, vary. It is also to be understood that the terminology used herein is for the purpose of describing particular embodiments only, and is not intended to be limiting. Further, unless defined otherwise, all technical and scientific terms used herein have the same meaning as commonly understood by one of ordinary skill in the art to which this invention pertains. In describing and claiming the present invention, the following terminology and grammatical variants will be used in accordance with the definitions set out below.

"Renal cell carcinoma" or "RCC" refers to carcinoma of the renal parenchyma. RCC is also often identified as renal cancer, "hypemephroma", or adenocarcinoma of the kidney. There are four main types of renal cell carcinoma, namely, clear cell type, granular cell type, mixed granular and clear cell type, and spindle cell type.

The terms "carbonic anhydrase IX" and "CAIX" are herein considered to be synonymous with "CA9", "MN", and "G250". The G250 antigen has been sequenced and revealed by database analysis to be homologous to the MN/CAIX antigen, a tumour-associated antigen originally identified in HeLa cells (Pastorek et al. (1994) "Cloning and characterization of MN, a human tumor associated protein with a domain homologous to carbonic anhydrase and a putative helix-loop-helix DNA binding segment," Oncogene 9:2877-2888 and Oosterwijk et al. (1996) "Molecular characterization of the renal cell carcinoma associated antigen G250," Proc Amer Assoc Cancer Res 37:461). This antigen (MN/CAIX/CA9/G250) is a plasma membrane glycoprotein with an apparent molecular weight of 54/58 kDa, detectable in several types of malignancies; e.g. cervical and ovarian cancer (Liao et al. et al. (1994) "Identification of the MN antigen as a diagnostic biomarker of cervical intraepithelial squamous and glandular neoplasia and cervical carcinomas," Am J Pathol 145:598-609), renal cancer (Oosterwijk et al. (1986) "Immunohistochemical analysis of monoclonal antibodies to renal antigens," Am J Pathol 123:301-309), colorectal cancer (Saarnio et al. (1997) "Immunohistochemical study of colorectal tumors for expression of a novel transmembrane carbonic anhydrase, MN/CA IX, with potential value as a marker of cell proliferation," Am J Pathol 153:279-285), oesophageal cancer (Turner et al. (1997) "MN antigen expression in normal, preneoplastic, and neoplastic esophagus: a clinicopathological study of a new cancer-associated biomarker," Human Pathol 28:740-744), bladder cancer (Uemura et al. (1997) "Expression of tumor-associated antigen MN/G250 in urologic carcinoma: potential therapeutic target," J Urol (Suppl) 157:377), but not in the normal tissues except alimentary tract, which indicates that the CAIX protein is associated with tumorigenicity. Sequential analysis has demonstrated that the gene (MN/CAIX/CA9/G250) is a novel member of the carbonic anhydrase (CA) family and MN/CAIX/G250 is considered to be the only tumor-associated CA isoenzyme. See, e.g., U.S. Pat. No. 6,297,051, entitled "MN GENE AND PROTEIN" issued Oct. 2, 2001 to Zavada et al., which is incorporated by reference in its entirety for all purposes. The coding sequence of CAIX is set forth in SEQ ID NO:1 and the corresponding protein sequence in SEQ ID NO:2.

The terms "polypeptide", "peptide", and "protein" are used interchangeably herein to refer to a polymer of amino acids that are covalently bound by peptide linkages. The terms "polypeptide", "peptide", and "protein" include glycoproteins as well as non-glycoproteins.

"Antibody" refers to a polypeptide substantially encoded by at least one immunoglobulin gene or fragments of at least one immunoglobulin gene, that can participate in specific binding with a ligand. The term includes naturally-occurring forms, as well as fragments and derivatives. Fragments within the scope of the term as used herein include those produced by digestion with various peptidases, such as Fab, Fab' and F(ab)'2 fragments, those produced by chemical dissociation, by chemical cleavage, and recombinantly, so long as the fragment remains capable of specific binding to a target molecule, such as a host cell protein. Typical recombinant fragments, as are produced, e.g., by phage display, include single chain Fab and scFv ("single chain variable region") fragments. Derivatives within the scope of the term include antibodies (or fragments thereof) that have been modified in sequence, but remain capable of specific binding to a target molecule, including interspecies chimeric and humanized antibodies. As used herein, antibodies can be produced by any known technique, including harvest from cell culture of native B lymphocytes, hybridomas, recombinant expression systems, by phage display, or the like.

"Antigen" refers to a ligand that can be bound by an antibody. An antigen need not be immunogenic. The portions of the antigen that make contact with the antibody are denominated "epitopes".

"Prognosis" refers to a forecast as to the probable outcome of a disease state, a determination of the prospect as to recovery from a disease as indicated by the nature and symptoms of a case, the monitoring of the disease status of a patient, the monitoring of a patient for recurrence of disease, and/or the determination of the preferred therapeutic regimen for a patient.

"Quantification percentage" refers to a CAIX expression score that includes the percentage of a sample (e.g., a target tissue or cellular sample, such as a sample from a renal tumor, a sample from a metastatic lesion derived from a metastitic lesion, and/or the like) that has positive CAIX expression. In preferred embodiments, the quantification percentage of a sample refers a CAIX expression score that includes the extent of staining or staining percentage (e.g., the percentage of cells in a sample that stain positively for CAIX, etc.). In certain embodiments, other factors such as staining intensity and the percentage staining at maximal staining intensity are also included in a CAIX expression score for a particular sample. For example, as illustrated in an example provided below, survival tree analysis of CAIX scoring information from the analyzed tissue arrays identified that a staining percentage of 85% was an ideal cutoff for stratification for patient survival. Staining percentages>85%, irrespective of intensity, were considered high CAIX staining, whereas those ≤85% were considered low CAIX staining.

II. Renal Cell Carcinoma Prognosis and Therapy Selection

Renal cell carcinoma (RCC) accounts for about 85 percent of all primary renal neoplasms, and metastatic RCC has a poor prognosis and an unpredictable course. Further, prior to the present invention there were no molecular markers that could reliably predict RCC outcome, as the relationship between carbonic anhydrase IX (CAIX) expression and RCC survivorship was unknown. The present invention demonstrates, inter alia, that the kidney cancer marker CAIX is associated with progression and survival. For example, CAIX reflects significant changes in tumor biology that can be used to predict clinical outcome and to identify high risk patients in need of, e.g., adjuvant immunotherapy and CAIX-targeted therapies.

In particular, the invention provides methods of aiding in a renal cell carcinoma prognosis. The methods include quantifying expressed CAIX (e.g., CAIX polypeptides, a fragment of a CAIX polypeptide, an mRNA that encodes a CAIX polypeptide, a cDNA corresponding to an mRNA that encodes a CAIX polypeptide, or the like), if any, present in samples derived from a subject diagnosed with renal cell carcinoma. The quantified CAIX expression data is correlated with a probability of a renal cell carcinoma prognosis (e.g., a positive or negative prognosis) for the subject. In preferred embodiments, expressed CAIX polypeptides are quantified in the samples derived from the subject. These methods can be used to detect tumors, quantitate their growth, and aid in the diagnosis and prognosis of disease. These methods can also be used to detect the presence of cancer metastasis, as well as confirm the absence or removal of all tumor tissue following surgery, cancer chemotherapy and/or radiation therapy. They can further be used to monitor cancer chemotherapy and tumor reappearance.

The CAIX antigen is typically quantitated in mammalian samples, which are preferably human samples. Such samples optionally include tissue specimens, body fluids (e.g., urine), tissue extracts, cells, cell lysates and cell extracts, among other samples. In preferred embodiments, samples are derived from renal tumors and/or metastatic lesions derived from renal tumors.

The CAIX antigen can be detected and quantified by various techniques. In preferred embodiments, CAIX is detected and quantified by immunohistochemical staining (e.g., using tissue arrays or the like). Preferred tissue specimens to assay by immunohistochemical staining, for example, include cell smears, histological sections from biopsied tissues or organs, and imprint preparations among other tissue samples. An exemplary immunohistochemical staining protocol is described further below. Such tissue specimens can be variously maintained, for example, they can be fresh, frozen, or formalin-, alcohol- or acetone- or otherwise fixed and/or paraffin-embedded and deparaffinized. Biopsied tissue samples can be, for example, those samples removed by aspiration, bite, brush, cone, chorionic villus, endoscopic, excisional, incisional, needle, percutaneous punch, and surface biopsies, among other biopsy techniques.

As mentioned, many formats for detection and quantification of the CAIX antigen are optionally adapted for use with the methods of the present invention. Certain exemplary techniques include, e.g., Western blotting, immunoassays (e.g., radioimmunoassays (RIAs), enzyme immunoassays (EIAs), etc.), immunohistochemical staining, immunoelectron and scanning microscopy using immunogold, ELISAs, competitive EIA or dual antibody sandwich assays, among other assays commonly known in the art.

Representative of one type of ELISA test for CAIX antigen is a format in which a microtiter plate is coated with antibodies made to CAIX polypeptides or antibodies made to whole cells expressing CAIX proteins, and to this is added a patient sample, for example, a tissue or cell extract. After a period of incubation permitting any antigen to bind to the antibodies, the plate is washed and another set of anti-CAIX antibodies which are linked to an enzyme is added, incubated to allow reaction to take place, and the plate is then rewashed. Thereafter, enzyme substrate is added to the microtiter plate and incubated for a period of time to allow the enzyme to work on the substrate, and the adsorbance of the final preparation is measured. A large change in absorbance typically indicates a positive result.

It is also apparent to one skilled in the art of immunoassays that CAIX polypeptides can be used to detect and/or quantitate the presence of CAIX antigen in the body fluids, tissues and/or cells of patients. In one such embodiment, a competition immunoassay is used, wherein the CAIX protein is labeled and a body fluid is added to compete with the binding of the labeled CAIX polypeptide to antibodies specific to CAIX polypeptide.

As another exemplary embodiment, an immunometric assay may be used in which a labeled antibody made to a CAIX protein is used. In such an assay, the amount of labeled antibody which complexes with the antigen-bound antibody is directly proportional to the amount of CAIX antigen in the sample.

Antibodies suitable for use in certain embodiments of the methods described herein may be prepared by conventional methodology and/or by genetic engineering. Antibody fragments may be genetically engineered, preferably from the variable regions of the light and/or heavy chains ($V_H$ and $V_L$), including the hypervariable regions, and still more preferably from both the $V_H$ and $V_L$ regions. For example, the term "antibodies" as used herein includes polyclonal and monoclonal antibodies and biologically active fragments thereof including among other possibilities "univalent" antibodies (Glennie et al. (1982) *Nature* 295:712); Fab proteins including Fab' and F(ab')$_2$ fragments whether covalently or noncovalently aggregated; light or heavy chains alone, preferably variable heavy and light chain regions ($V_H$ and $V_L$ regions), and more preferably including the hypervariable regions (otherwise known as the complementarity determining regions (CDRs) of the $V_H$ and $V_L$ regions); $F_c$ proteins; "hybrid" antibodies capable of binding more than one antigen; constant-variable region chimeras; "composite" immunoglobulins with heavy and light chains of different origins; "altered" antibodies with improved specificity and other characteristics as prepared by standard recombinant techniques and also by oligonucleotide-directed mutagenesis techniques (Dalbadie-McFarland et al. (1982) *Proc. Natl. Acad. Sci. USA* 79: 6409).

The antibodies useful according to this invention to identify CAIX polypeptides can be labeled in essentially any manner, for example, with enzymes such as horseradish peroxidase (HRP), fluorescent compounds, or with radioactive isotopes such as, $^{125}$I, among other labels.

Bispecific antibodies that are optionally adapted for use in the present invention can be produced by chemically coupling two antibodies of the desired specificity. Bispecific MAbs can preferably be developed by somatic hybridization of 2 hybridomas. Bispecific MAbs for targeting CAIX protein and another antigen can be produced by fusing a hybridoma that produces CAIX-specific MAbs with a hybridoma producing MAbs specific to another antigen. For example, a cell (a quadroma), formed by fusion of a hybridoma producing a CAIX-specific MAb and a hybridoma producing an anti-cytotoxic cell antibody, will produce hybrid antibody having specificity of the parent antibodies. See., e.g., Immunol. Rev. (1979); Cold Spring Harbor Symposium Quant. Biol., 41: 793 (1977); van Dijk et al., Int. J. Cancer, 43: 344-349 (1989). Thus, a hybridoma producing a CAIX-specific MAb can be fused with a hybridoma producing, for example, an anti-T3 antibody to yield a cell line which produces a CAIX/T3 bispecific antibody which can target cytotoxic T cells to CAIX-expressing tumor cells.

Although representative hybridomas of use in practicing this invention are formed by the fusion of murine cell lines, human/human hybridomas (Olsson et al. (1980) *Proc. Natl. Acad. Sci. USA* 77:5429) and human/murine hybridomas (Schlom et al. (1980) *Proc. Natl. Acad. Sci. USA* 77:6841; Shearman et al. (1991) *J. Immunol.* 146: 928-935; and Gorman et al. (1991) *Proc. Natl. Acad. Sci. USA* 88:4181-4185) can also be prepared among others.

Monoclonal antibodies for use in the methods of this invention may be obtained by methods well known in the art. See, e.g., Galfre and Milstein, "Preparation of Monoclonal Antibodies: Strategies and Procedures," in Methods in Enzymology: Immunochemical Techniques, 73: 1-46 [Langone and Vanatis (eds); Academic Press (1981)]. See also, Milstein and Kohler (1975) *Nature* 256:495-497. Monoclonal antibodies specific for this invention can be prepared by immunizing appropriate mammals, preferably rodents, rabbits or mice, with an appropriate immunogen, for example, MaTu-infected HeLa cells, CAIX fusion proteins, or CAIX proteins attached to a carrier protein, if necessary.

Representative MAbs of use in this invention include MAbs M75, MN9, MN12 and MN7. For example, Monoclonal antibody M75 (MAb M75) is produced by mouse lymphocytic hybridoma VU-M75, which was initially deposited in the Collection of Hybridomas at the Institute of Virology, Slovak Academy of Sciences (Bratislava, Slovakia) and was deposited under ATCC Designation HB 11128 on Sep. 17, 1992 at the American Type Culture Collection (ATCC). The production of hybridoma VU-M75 is described in Zavada et al., International Publication No. WO 93/18152. Mab M75 recognizes both the nonglycosylated GST-MN fusion protein and native CAIX protein as expressed in CGL3 cells equally well. The M75 MAb recognizes both native and denatured forms of the CAIX protein (Pastorekova et al. (1992) *Virology* 187:620-626).

Antibodies employed in assays may be labeled or unlabeled. Unlabeled antibodies may be employed in agglutination; labeled antibodies may be employed in a wide variety of assays, employing a wide variety of labels known in the art. Suitable detection means include the use of labels such as radionuclides, enzymes, coenzymes, fluorescers, chemiluminescers, chromogens, enzyme substrates or co-factors, enzyme inhibitors, free radicals, particles, dyes and the like. Such labeled reagents may be used in a variety of well known assays (referred to above), such as radioimmunoassays, enzyme immunoassays, e.g., ELISA, fluorescent immunoassays, and the like. See, e.g., U.S. Pat. Nos. 3,766,162; 3,791, 932; 3,817,837; and 4,233,402.

An exemplary immunohistochemical staining protocol using a Dako staining kit (Dako Corporation, Carpenteria, Calif.) includes dewaxing, rehydrating and blocking sample sections to remove non-specific reactivity as well as endogenous peroxidase activity. Sections can then be incubated with dilutions of the M75 monoclonal antibody. After the unbound M75 is removed by rinsing the section, the section can be sequentially reacted with a biotinylated antimouse IgG antibody and streptavidin conjugated to horseradish peroxidase; a rinsing step can be included between those two reactions and after the second reaction. Following the last rinse, the antibody-enzyme complexes can be detected by reaction with an insoluble chromogen (diaminobenzidine) and hydrogen peroxide. A positive result is indicated by the formation of an insoluble reddish-brown precipitate at the site of the primary antibody reaction. The sections can then be rinsed, counterstained with hematoxylin, dehydrated and cover slipped. Thereafter, the sections can be examined using standard light microscopy. A deposit of a reddish brown precipitate over the plasma membrane is evidence that the M75 antibody has bound to a CAIX antigen in the tissue. A known positive control (e.g., CGL3) can be stained to validate the assay. Section thickness should be taken into consideration when comparing staining intensities, as thicker sections produce greater staining intensity independent of other assay parameters.

In certain embodiments of the invention, mRNA that encodes a CAIX polypeptide is optionally detected in a sample and correlated with a prognosis for a patient. Detection of RNA transcripts may be achieved by Northern blotting, for example, in which a preparation of RNA is run on a denaturing agarose gel, and transferred to a suitable support, such as activated cellulose, nitrocellulose or glass or nylon membranes. Radiolabelled cDNA or RNA is then hybridized to the preparation, washed and analyzed by autoradiography. In situ hybridization visualization may also be employed in which a radioactively labelled antisense cRNA probe is hybridized with a thin section of a biopsy sample, washed, cleaved with RNase and exposed to a sensitive emulsion for autoradiography. The samples may be stained with haematoxylon to demonstrate the histological composition of the sample, and dark field imaging with a suitable light filter illuminates the developed emulsion. Non-radioactive labels such as digoxigenin may also be used.

General texts describing additional molecular biological techniques useful herein, including the preparation of antibodies include Berger and Kimmel, *Guide to Molecular Cloning Techniques, Methods in Enzymology*, Vol. 152, Academic Press, Inc., Sambrook et al., *Molecular Cloning—A Laboratory Manual* (2nd Ed.), Vol. 1-3, Cold Spring Harbor Laboratory (1989), *Current Protocols in Molecular Biology*, F. M. Ausubel et al. (Eds.), Current Protocols, a joint venture between Greene Publishing Associates, Inc. and John Wiley & Sons, Inc. (supplemented through 2000), Harlow et al., *Monoclonal Antibodies: A Laboratory Manual*, Cold Springs Harbor Laboratory Press (1988), Paul (Ed.), *Fundamental Immunology*, Lippincott Williams & Wilkins (1998), and Harlow et al., *Using Antibodies: A Laboratory Manual*, Cold Spring Harbor Laboratory Press (1998).

Following detection and quantitation of CAIX in one or more samples from a subject diagnosed with RCC, the CAIX expression data is correlated with clinical and/or pathological data to arrive at prognostic information for the patient. Data generated by the methods described herein is optionally analyzed using any suitable technique. Statistical analysis of data and more particularized correlations are described in greater detail in an example provided below. In one embodiment, data is analyzed with the use of a logic device, such as a programmable digital computer that is included, e.g., as part of a system. The computer generally includes a computer readable medium that stores logic instructions of the system software. Certain logic instructions are typically devoted to memory for receiving quantified CAIX expression data derived from a subject diagnosed with renal cell carcinoma. The computer also typically includes logic instructions for determining closeness-of-fit between the quantified CAIX expression data and database entries, which entries correspond to clinical and/or pathological data for a population of renal cell carcinoma patients to thereby correlate the quantified CAIX expression data with a probability of a renal cell carcinoma prognosis for the subject.

In preferred embodiments, the quantified CAIX expression data is in a computer-readable form suitable for use in database queries. For example, a database query generally includes operating a programmable computer that comprises at least one database and executing an algorithm that determines closeness-of-fit between the computer-readable quantified CAIX expression data and database entries, which entries correspond to clinical and/or pathological data for a population of renal clear cell carcinoma patients to thereby correlate the quantified CAIX expression data with the probability of the renal clear cell carcinoma prognosis for the subject. In some embodiments, the algorithm includes an artificial intelligence algorithm or a heuristic learning algorithm. For example, the artificial intelligence algorithm optionally includes one or more of, e.g., a fuzzy logic instruction set, a cluster analysis instruction set, a neural network, a genetic algorithm, or the like.

The present invention also provides a computer program product comprising a computer readable medium having one or more logic instructions. The computer readable medium includes logic instructions for (a) receiving quantified CAIX expression data derived from a subject diagnosed with renal cell carcinoma. The computer readable medium also includes logic instructions for (b) determining closeness-of-fit between the quantified CAIX expression data and database entries, which entries correspond to clinical and/or pathological data for a population of renal cell carcinoma patients to thereby correlate the quantified CAIX expression data with a probability of a renal cell carcinoma prognosis for the subject. Furthermore, the computer readable medium optionally includes, e.g., a CD-ROM, a floppy disk, a tape, a flash memory device or component, a system memory device or component, a hard drive, or a data signal embodied in a carrier wave.

The present invention will hereinafter be described in further detail by example. However, it should be borne in mind that this invention is by no means limited to or by the example.

III. Example

To investigate the importance and clinical significance of CAIX expression, tissue microarrays (Kononen et al. (1998) "Tissue microarrays for high-throughput molecular profiling of tumor specimens," *Nat. Med.* 4:844-847) were used for high throughput molecular profiling of RCC tumor specimens based on their CAIX expression. Furthermore, a RCC database at the University of California at Los Angeles (UCLA) with 1200 patients containing more than 263 clinical variables for each patient were also utilized. The clinical information from this data resource was used to evaluate the association of CAIX expression with clinical outcome.

Patients and Methods

Patients

The study cohort consisted of 321 patients who underwent a radical or partial nephrectomy for clear cell RCC at UCLA between 1989 and 2000. Following study protocol (KCP 99-233) approval by the UCLA Institutional Review Board, a retrospective study was performed with outcome assessment based on chart review of clinical and pathologic data. The median age was 62 years (27-89 years), and the male to female ratio was 2:1. The median follow-up for patients who died (N=170) from an RCC-related cause was 14 months (1.3-101 months) and for all survivors was 45 months (0.3-117 months). The diagnosis of metastatic disease was determined at initial presentation. IL-2-based immunotherapy was administered to 86 patients, 70 of who presented with metastatic disease, with the remaining 16 developing recurrent disease after nephrectomy for initially localized RCC.

Stage was determined according to the 1997 Union Internationale Contre le Cancer tumor-node-metastasis classification of malignant tumors (Sobin et al. (1997) "TNM Classification of Malignant Tumors, 5 Ed.," Union Internationale Contre le Cancer and the American Joint Committee on Cancer, *Cancer (Phila.)* 80:1803-1804). T, N, and M stages were determined by clinical and/or pathologic data. ECOG PS and metastatic status was determined at initial presentation (Roila et al. (1991) "Intra and interobserver variability in cancer patients' performance status assessed according to Karnofsky and ECOG scales," *Ann. Oncol.* 2:437-439).

Fifteen patients had concurrent resection of a metastatic lesion at the time of nephrectomy for the primary tumor. Histopathological evaluation confirmed that the metastatic lesion arose from the same histological type as the primary kidney tumor.

Tissue Array Construction

Archival tumor specimens from the cohort of 321 patients and 15 metastatic lesions were obtained from the Department of Pathology at the UCLA Medical Center. All tumors were of the clear cell subtype according to Union Internationale Contre le Cancer guidelines and were staged according to the 1997 tumor-node-metastasis classification and graded according to the Fuhrman grading scheme by a single pathologist (Sobin et al. (1997) *Cancer (Phila.)* 80:1803-1804 (above) and Fuhrman et al. (1982) "Prognostic significance of morphologic parameters in renal cell carcinoma,"

*Am. J. Surg. Pathol.* 6:655-663). Three core tissue biopsies, 0.6 mm in diameter, were taken from selected morphologically representative regions of each paraffin-embedded renal or metastatic tumor and precisely arrayed using a custom-built instrument as described previously (Kononen et al. (1998) *Nat. Med.* 4:844-847 (above)). An additional core tissue biopsy was taken from a morphologically normal-appearing region of each tumor. Sections of 4-μm thickness of each tissue array block were transferred to glass slides using the paraffin sectioning aid system (adhesive coated slides PSACS4x, adhesive tape, UW lamp; Instrumedics Inc., Hackensack, N.J.) to support the cohesion of 0.6-mm array elements. Quality control was assessed on each block by H&E staining after every five consecutive sections to confirm the grade and histological type of each tissue core spot.

Immunohistochemistry

The mouse monoclonal antibody (M75) used to detect the CAIX protein has been described previously (Zavada et al. (1993) "Expression of MaTu-MN protein in human tumor cultures and in clinical specimens," *Int. J. Cancer* 54:268-274 and Liao et al. (1994) "Identification of the MN antigen as a diagnostic biomarker of cervical intraepithelial squamous and glandular neoplasia and cervical carcinomas," *Am. J. Pathol.* 145:598-609). Immunohistochemical staining of tissue sections with anti-CAIX antibody was done using a peroxidase technique with antigen retrieval using heat treatment, as previously described using the Dako staining systems (Dako Corporation, Carpenteria, Calif.; Liao et al. (1994) *Am. J. Pathol.* 145:598-609 (above)). The CAIX primary antibody was used at a 1:10,000 dilution. Semiquantitative assessment of the antibody staining was performed by a single pathologist blinded to the clinicopathological variables. Staining intensity was based on a 4-point scale from 0 to 3. The extent of staining was recorded as a percentage of the target tissue sample that had positive CAIX expression. Each spot was scored based on the staining intensity, the percentage of positive cells, and the percentage staining at maximal staining intensity. There were three spots/patient specimen. The overall score used for subsequent statistical analysis was the pooled mean from three spots of the same tumor. A score of zero was given to tissue spots that had no evidence of specific immunostaining.

Statistical Analysis

The primary outcome of interest was disease-specific survival (DSS) from the time of nephrectomy to demise or to last follow-up. The default settings of the recursive partitioning function in S-Plus (Insightful Corp.) statistical analysis software were used for survival tree analysis to find appropriate cut-offs for classifying patients according to amount of CAIX expression. The Kaplan-Meier method was used to estimate DSS (Kaplan et al. (1958) "Nonparametric estimation from incomplete observations," *J. Am. Stat. Assoc.* 53:457-481); log-rank analysis was applied to test the difference between stratified survival functions. The Cox proportional hazards model (Cox et al., *Analysis of survival data*, Chapman and Hall (1990)) was used to test the statistical independence and significance of CAIX expression in predicting the risk of patient death based on a variety of potential prognostic factors (Kalbfleisch et al., *The statistical analysis of failure time data*, John Wiley (1980)). Logistic regression was used to quantify the area under the ROC. The binomial test was used to determine statistical significance of CAIX expression in the primary tumor compared with the metastasis. All Ps were two sided, and $P<0.05$ was considered significant. Statistical analyses were performed, and graphs were constructed using Stata statistical analysis software version 7.0 (Stata Corp, College Station, Tex.).

Results

The clinical characteristics of the 321 patients (216 men and 105 women) at the time of nephrectomy for clear cell RCC are summarized in Table 1. Among these patients, the median age was 61 years, the median tumor size was 7 cm and 46% had metastatic disease at the time of presentation. The median follow-up time of all patients who died of a cancer-related death was 14 months (range, 1.3-101 months) and for all survivors was 45 months (range, 0.3-117 months).

TABLE 1

|  | Overall (N = 321) | CAIX (No. of patients) | | | |
|---|---|---|---|---|---|
|  |  | Negative | Positive | Low ≤85% | High >85% |
| Gender |  |  |  |  |  |
| Male | 216 |  |  |  |  |
| Female | 105 |  |  |  |  |
| Age, yr |  |  |  |  |  |
| Mean | 60.4 ± 11.7 |  |  |  |  |
| Median | 61.6 |  |  |  |  |
| Range | 27-89 |  |  |  |  |
| Tumor size, cm |  |  |  |  |  |
| Median | 7 | 5 | 7 | 7.5 | 6.5 |
| Mean | 7.3 ± 3.8 | 6.5 ± 4.6 | 7.3 ± 3.7 | 8.1 ± 3.4 | 7.1 ± 3.6 |
| Range | 0.8-18.0 |  |  |  |  |
| Metastasis |  |  |  |  |  |
| No | 172 | 15 | 157 | 32 | 140 |
| Yes | 149 | 6 | 143 | 34 | 115 |
| T" stage |  |  |  |  |  |
| 1 | 114 | 13 | 101 | 22 | 92 |
| 2 | 39 | 2 | 37 | 8 | 31 |
| 3 | 150 | 6 | 144 | 29 | 121 |
| 4 | 18 | 0 | 18 | 7 | 11 |

TABLE 1-continued

|  | Overall (N = 321) | CAIX (No. of patients) | | | |
|---|---|---|---|---|---|
|  |  | Negative | Positive | Low ≤85% | High >85% |
| Grade |  |  |  |  |  |
| 1 | 38 | 3 | 35 | 6 | 32 |
| 2 | 151 | 10 | 141 | 32 | 119 |
| 3 | 110 | 5 | 105 | 20 | 90 |
| 4 | 22 | 3 | 19 | 8 | 14 |
| Nodes |  |  |  |  |  |
| 0 | 272 | 17 | 261 | 50 | 228 |
| 1 | 14 | 1 | 13 | 5 | 9 |
| 2 | 23 | 3 | 20 | 9 | 14 |
| ECOG ps |  |  |  |  |  |
| 0 | 115 | 5 | 110 | 15 | 100 |
| 1 | 190 | 15 | 175 | 46 | 144 |
| 2 | 13 | 1 | 12 | 5 | 8 |
| 3 | 1 | 0 | 1 | 0 | 1 |
| IL-2-based immunotherapy | 86 | 1 | 85 | 14 | 72 |
| Overall response | 22 |  |  | 2 | 20 |
| Complete response | 7 |  |  | 0 | 7 |
| No response | 27 |  |  | 7 | 20 |
| Stable disease | 27 | 1 |  | 4 | 23 |
| NE | 3 |  |  | 1 | 2 |
| Duration median follow-up, months |  |  |  |  |  |
| Cancer-related deaths | 14 (1.3-101) |  |  |  |  |
| All survivors | 44 (0.3-117) |  |  |  |  |
| Relapses | 38 |  |  |  |  |
| Deaths | 170 |  |  |  |  |

<sup>a</sup>T, tumor;
NE, not evaluable.

CAIX Expression in Relation to Clinicopathological Variables

CAIX expression was seen in 94% (301 of 321) of tumor specimens. CAIX staining was predominantly found on the plasma membrane and varied according to the proportion of the target tissue in the core that stained positively (FIG. 1A). The staining intensity staining was strong with minimal variation. Tissue core biopsies taken from a morphologically normal appearing region of each tumor specimen were uniformly negative for CAIX whereas tumor regions predominantly stained intensely.

Survival tree analysis of CAIX scoring information from the tissue arrays identified that a staining percentage of 85% was an ideal cutoff for stratification for patient survival. Staining percentages>85%, irrespective of intensity, were considered high CAIX staining, whereas those ≤85% were considered low CAIX staining (FIG. 1A). Only 4.7% (N=15) of patients in the cohort had staining percentages within the range of 80-90% (FIG. 1B). Most of the patients (N=255, 79%) had >85% CAIX staining, whereas 21% (N=66) had ≤85% CAIX staining. Survival of patients with CAIX-negative staining (0%) did not differ statistically from patients with low (≤85%) CAIX staining (data not shown). For patients with metastatic RCC, Kaplan-Meier estimated DSS showed that high CAIX was associated with a median survival of 24.8 months, whereas low CAIX had a median survival of only 5.5 months (P=0.001; FIG. 1C).

Figure 2:
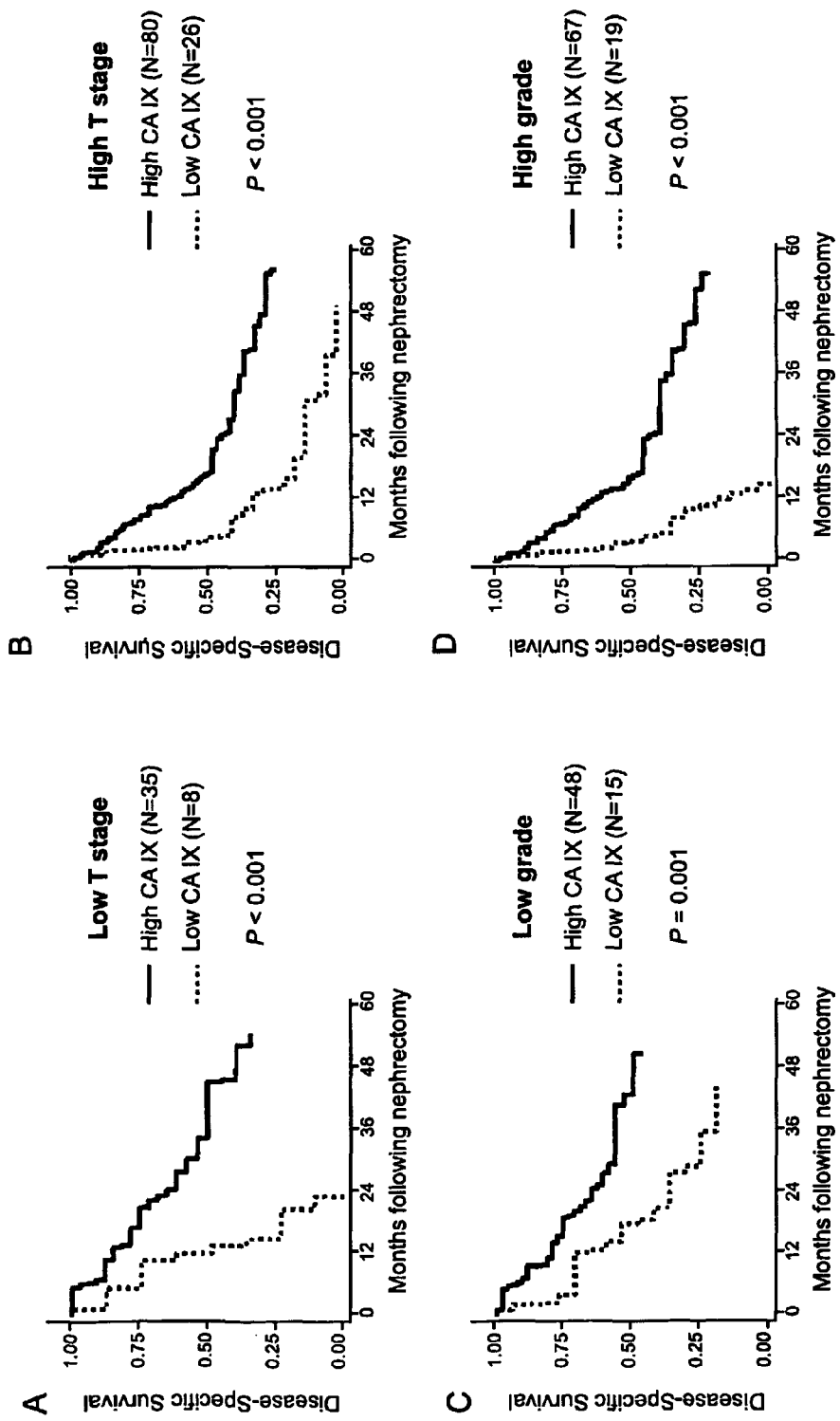
FIGS. 2A-D are data graphs (abscissa—months following nephrectomy; ordinate—DSS) that show DSS in patients with metastatic clear carcinoma. More specifically, Kaplan-Meier estimates according to CAIX expression for (FIG. 2A) low T stage (stages 1 and 2), (FIG. 2B) high T stage (stages 3 and 4), (FIG. 2C) low grade (grades 1 and 2), and (FIG. 2D) high grade (grades 3 and 4) are shown in which N=number of patients.

For patients diagnosed with metastatic disease at the time of initial presentation, CAIX expression provided important additional prognostic information when DSS was analyzed according to T stage and Fuhrman grade. Table 2 lists the median DSS (months) for patients with metastatic clear cell carcinoma when stratified according too high or low CAIX staining. High CAIX expression predicted a better prognosis for both low and high T stage as shown by Kaplan-Meier estimates of DSS (FIGS. 2, A and B). Interestingly, patients with both low T stage and low CAIX staining had a significantly worse median survival time (12.2 months) than patients with both high T stage and high CAIX staining (16.7 months; P=0.032). Similarly, high CAIX staining demonstrated more favorable survival for both low- and high-grade tumors (FIGS. 2, C and D). The survival time for low-grade tumors with low CAIX expression was not statistically different from the survival time for high-grade tumors with high CAIX (median, 15.2 versus 16.3 months; P=0.119). No statistically significant associations were found between the level of CAIX expression and either T stage or grade for patients with metastatic disease.

TABLE 2

|  | Low CAIX | High CAIX | P |
|---|---|---|---|
| Metastasis | 5.5 | 24.8 | <0.001 |
| Low T stage (1 or 2) | 12.2 | 54.4 | <0.001 |
| High T stage (3 or 4) | 4.0 | 16.7 | <0.001 |
| Low grade (1 or 2) | 15.2 | 32.7 | 0.001 |
| High grade (3 or 4) | 3.9 | 16.3 | <0.001 |
| No nodes | 12.8 | 27.3 | <0.001 |
| Nodes > 0 | 2.9 | 12.5 | 0.009 |
| ECOG PS = 0 | 9.8 | 44.2 | 0.005 |
| ECOG PS > 0 | 4.8 | 21.2 | <0.001 |

Figure 3:
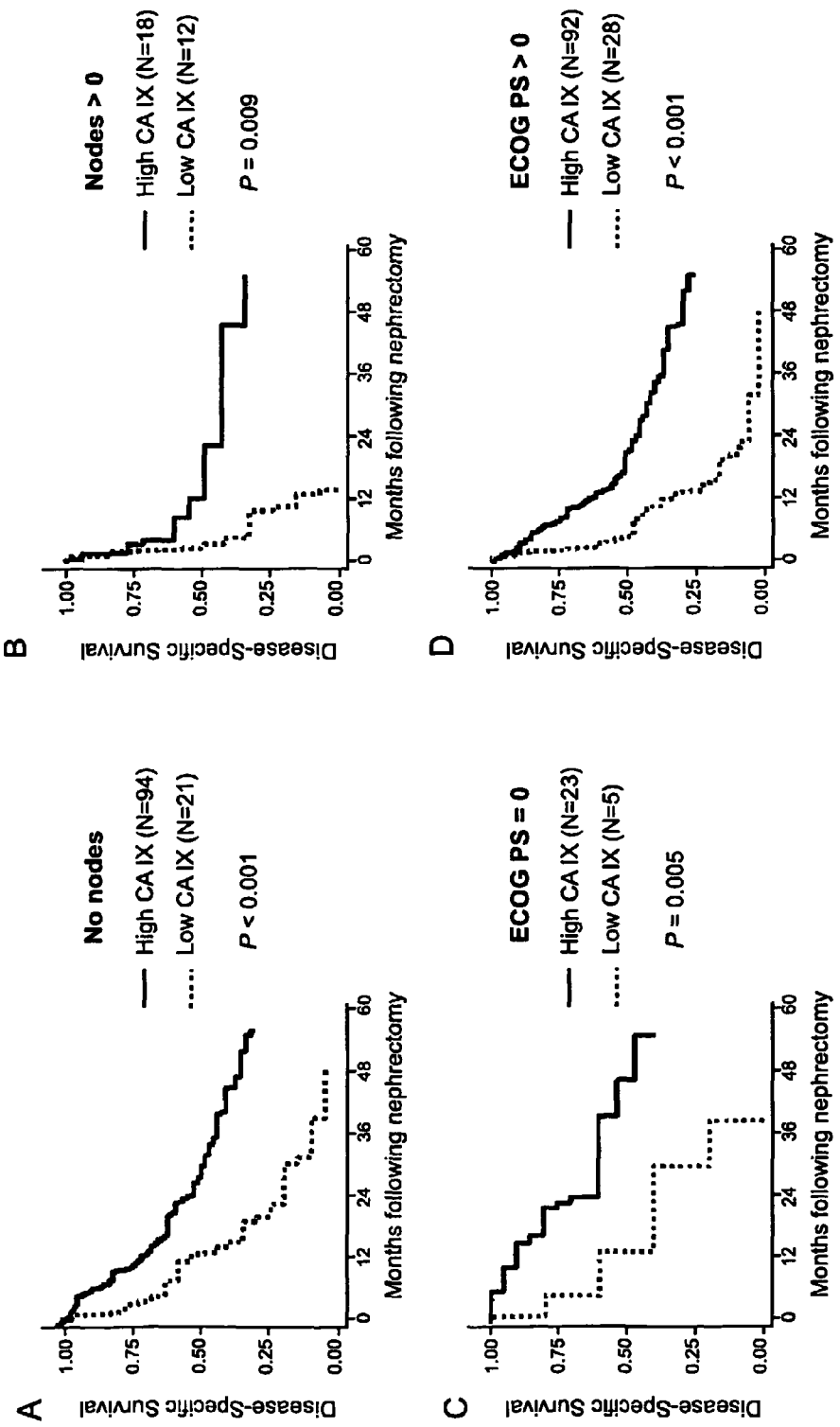
FIGS. 3A-D are data graphs (abscissa—months following nephrectomy; ordinate—DSS) that show DSS in patients with metastatic clear carcinoma. More specifically, Kaplan-Meier estimates according to CAIX expression for (FIG. 3A) no nodes, (FIG. 3B) nodes>0, (FIG. 3C) ECOG PS=0, and (FIG. 3D) ECOG PS>0 are shown, where ECOG PS is the Eastern Cooperative Oncology Group performance status and N=number of patients.

Prediction of DSS according to nodal status and ECOG PS could be additionally substratified by CAIX expression in patients with metastatic disease (FIG. 3). For patients with no nodal disease, high CAIX staining predicted better survival than low CAIX staining, median 27.3 months versus 12.8 months, respectively (P=0.001; FIG. 3A). Similarly, in patients with nodal disease (N=1 or N=2), high CAIX predicted a median survival of 12.5 versus 2.9 months for low CAIX (P=0.009; FIG. 3B). Interestingly, median survival for patients with both node-negative disease and low CAIX expression was not statistically different from the survival of patients with both node positive disease and high CAIX expression, 12.8 versus 12.5 months, respectively (P=0.103; Table 2). Higher CAIX expression also predicted a more favorable survival for patients with ECOG PS>0 with median survival of 44.2 months for high CAIX versus 9.8 months for low CAIX (P=0.005; FIG. 3C). For patients with ECOG PS>0, high CAIX staining predicted a median survival of 21.2 versus 4.8 months with low CAIX (P<0.001; FIG. 3D).

Figure 4:
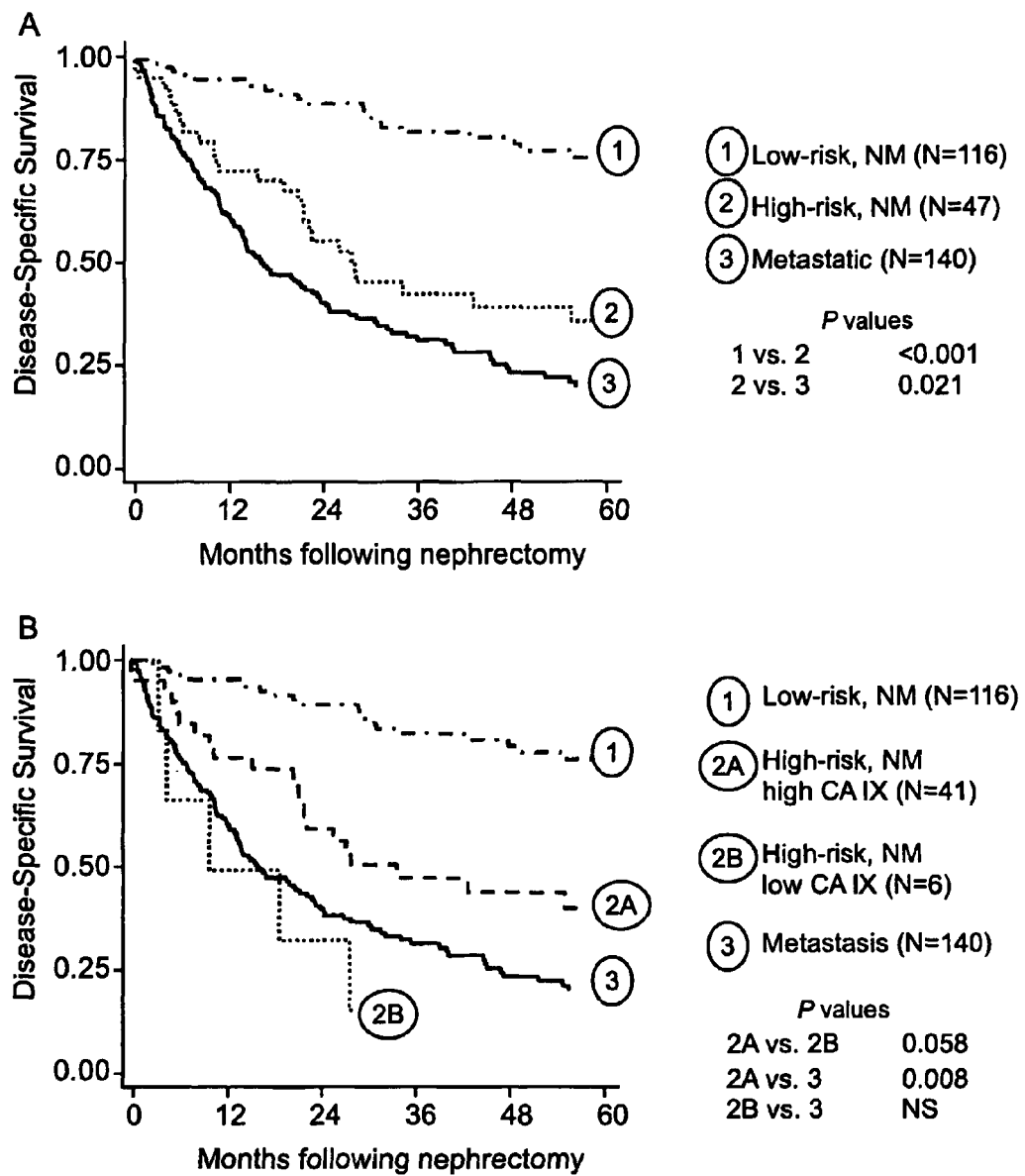
FIGS. 4 A and B are data graphs (abscissa—months following nephrectomy; ordinate—DSS) that show DSS in patients with localized and metastatic clear cell RCC. More specifically, Kaplan-Meier estimates according to (2A) high-risk (T stage≥3 and grade≥2) and low-risk (T stages≤2 and grade=1) patients with localized RCC and (2B) high-risk patients stratified by high and low CAIX expression are shown, where NM is nonmetastatic, N is the number of patients, and NS is not significant.

When patients with localized RCC were analyzed altogether, CAIX staining initially did not appear to stratify survival (P=0.25; FIG. 1C). However, using the Cox proportional hazards model, a subset of patients with localized RCC and no nodal or metastatic involvement was identified that could be additionally stratified by CAIX. Patients with T stage≥3 and grade≥2 were categorized as high risk for progression with a median survival of 28.5 months compared with low-risk patients (T stage≤2 and grade=1) who had a median survival of over 106 months (P<0.001; FIG. 4A). There were no missing data for T stage or grade for patients with localized RCC. The high-risk patients were statistically distinct from the patients with metastatic disease who had a median survival of 16.7 months (P=0.021; FIG. 4A). Stratification of high-risk patients according to high or low CAIX staining approached statistical significance (P=0.058; FIG. 4B) and was limited by small sample size (N=47). High-risk patients with high CAIX (N=41) had a median survival of 30.3 months. However, high-risk patients with low CAIX staining (N=6) had a worse prognosis with a median survival time of only 10 months and had a similar clinical outcome as patients with metastatic disease (16 months median survival). For low-risk nonmetastatic patients, CAIX status did not provide prognostic information. CAIX status also did not predict relapses (N=38) in patients with nonmetastatic disease, perhaps because of small sample size.

Relationship of CAIX to DSS

Univariate analysis of established prognostic factors and their relationship to DSS in metastatic disease confirmed that CAIX status, T stage, grade, nodal status, and ECOG PS were all statistically significant prognosticators (Table 3A). There were no apparent relationships between CAIX and other prognostic variables such as age, gender, and tumor size. In univariate analysis, CAIX status for high-risk nonmetastatic patients approached statistical significance (P=0.068) with hazard ratio of 2.53.

In multivariate Cox proportional hazards analysis, CAIX status was analyzed with T stage, grade, nodal status, and ECOG PS for their impact on DSS. For nonmetastatic disease, CAIX status was not an independent predictor of survival. However, for patients with metastatic disease, all of these covariates, except for nodal status, were significant independent predictors of DSS (Table 3B). Low CAIX staining in metastatic RCC was found to be independently associated with death from RCC, with a hazard ratio of 3.10 (P<0.001; 95% CI, 1.99-4.83). The addition of CAIX status to a logistic regression model consisting of T stage, grade, nodal status, and ECOG PS for metastatic disease increased the area under an ROC curve from 0.66 to 0.76 indicating improved prediction of survival. The time period used to calculate the ROC curve was 36 months. Furthermore, data censored for patients with >36 months follow-up and for patients who were alive but lost to follow-up. For the entire cohort of patients, 62% of patients with metastatic disease died from RCC by 36 months. The area under the ROC curve did not change when CAIX status was included for nonmetastatic disease.

TABLE 3

| A. Cox univariate analysis | | | |
|---|---|---|---|
| | Hazard ratio | 95% Cl | Significance |
| Variable | | | |
| CAIX, low expression | 3.17 | 2.07-4.86 | <0.001 |
| ECOG PS | 1.62 | 1.18-2.24 | 0.003 |
| Grade | 1.52 | 1.15-2.01 | 0.004 |
| Tumor stage | 1.44 | 1.12-1.87 | 0.005 |
| Nodal status | 1.32 | 1.02-1.71 | 0.033 |

| B. Cox multivariate analysis | | | |
|---|---|---|---|
| | Hazard ratio | 95% Cl | Significance |
| Variable | | | |
| CAIX, low expression | 3.10 | 1.99-4.83 | <0.001 |
| ECOG PS | 1.67 | 1.20-2.36 | 0.003 |
| Tumor stage | 1.37 | 1.04-1.79 | 0.023 |
| Grade | 1.37 | 1.03-1.83 | 0.032 |
| Nodal status | 1.15 | 0.88-1.52 | NS |

Relationship Between CAIX Expression in Primary Tumor and Metastatic Lesion

Figure 5:
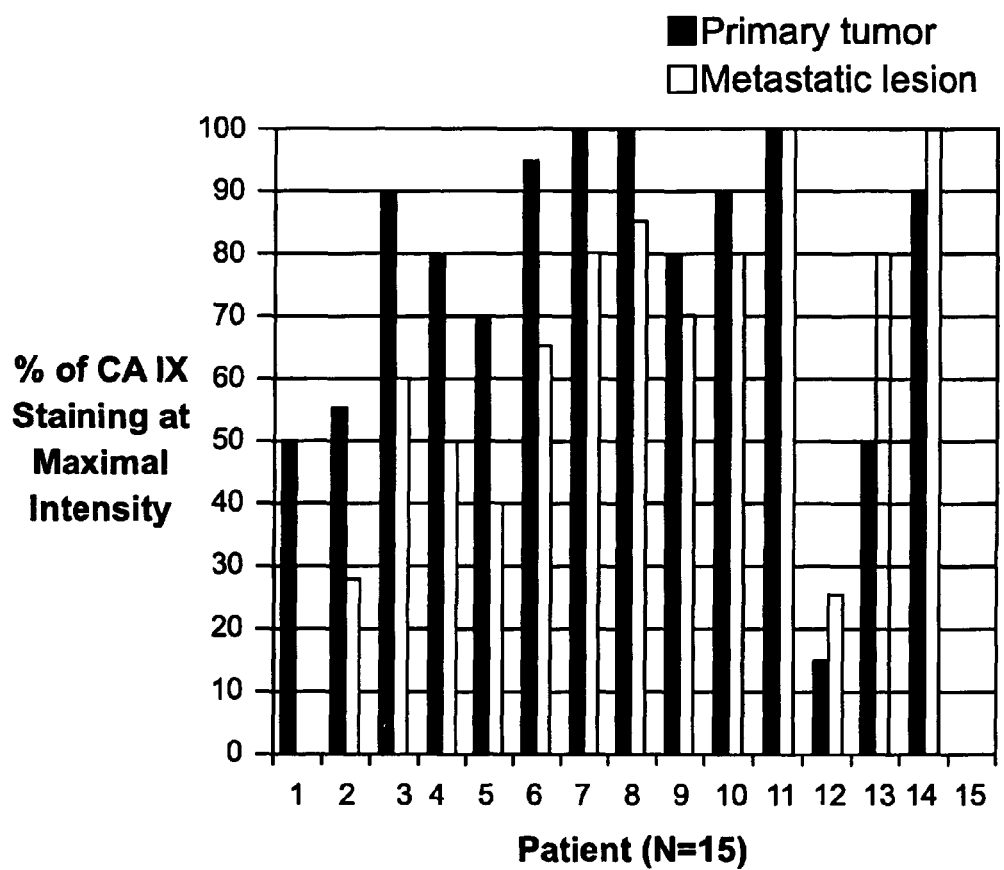
FIG. 5 is a data graph (abscissa—patient number (N=15); ordinate—% of CAIX staining at maximal intensity) that shows CAIX expression in the primary tumor and metastatic lesion. In particular.

To determine the effect on CAIX expression when a tumor metastasizes, the level of CAIX expression in the metastatic lesion and the primary tumor were compared. Fifteen patients had resection of a metastatic lesion (9 lymph nodes, 2 liver, 1 lung, 1 adrenal, 1 colon, and 1 chest wall) at the time of nephrectomy for RCC. The tumor specimens were compared based on the percentage staining at maximal intensity. CAIX expression appeared to be less in the metastatic lesion (3 of 13) compared with the primary tumor (FIG. 5). CAIX expression in both the primary tumor and metastasis was absent in 1 patient and equal in another. Overall, CAIX staining appeared greater in the primary tumor than in the metastatic lesion (P=0.036; binomial test).

Discussion

This analysis found that low CAIX expression was a predictor of worse survival in patients with advanced RCC. The relationship between low CAIX expression and poor prognosis has been shown in studies with cervical carcinoma (Brewer et al. (1996) "A study of biomarkers in cervical carcinoma and clinical correlation of the novel biomarker MN," *Gynecol. Oncol.* 63:337-344), colorectal carcinoma (Saarnio et al. (1998) "Immunohistochemical study of colorectal tumors for expression of a novel transmembrane carbonic anhydrase. MN/CA IX, with potential value as a marker of cell proliferation," *Am. J. Pathol.* 153:279-285), and esophageal cancer (Turner et al. (1997) "MN antigen expression in normal, preneoplastic, and neoplastic esophagus: a clinicopathological study of a new cancer-associated biomarker," *Hum. Pathol.* 28:740-744). In contrast, other studies have found that increased CAIX expression correlated with worse survival in cervical carcinoma (Loncaster et al. (2001) "Carbonic anhydrase (CA IX) expression, a potential new intrinsic marker of hypoxia: correlations with tumor oxygen measurements and prognosis in locally advanced carcinoma of the cervix," *Cancer Res.* 61:6394-6399), lung cancer (Giatromanolaki et al. (2001) "Expression of hypoxiainducible carbonic anhydrase-9 relates to angiogenic pathways and independently to poor outcome in non-small cell lung cancer," *Cancer Res.* 61:7992-7998), and breast cancer (Giatromanolaki et al. (2001) *Cancer Res.* 61:7992-7998 (above)). The reasons for these differences are unclear but may be related to whether CAIX expression reflects tumor progression or directly influences tumor behavior. Furthermore, in the analysis described herein, low CAIX status identified a subset of patients with high-risk localized RCC who had a clinical outcome similar to patients with metastatic disease. This group of patients would be excellent candidates for adjuvant immunotherapy trials.

Survival tree analysis used a method of recursive partitioning to define the 85% threshold for high and low CAIX staining that maximized the survival distributions between potential groups (Zhang et al., *Recursive partitioning in the health sciences*, p. 238, Springer-Verlag (1999)). The subsequent covariates were used in a Cox regression to obtain Ps. Similar statistical results were found when the CAIX threshold was lowered to 0% (e.g., positive or negative CAIX expression, P=0.008; data not shown), but this did not maximize the survival distributions. Furthermore, the range of 0-85% for the low CAIX group reflected a homogeneous population that was not able to be additionally stratified by smaller ranges (data not shown). The 15 cases within the range of 80-90%, which were not reliably separated into by the 85% cutoff, constituted only 4.7% of the cohort of 321 patients, whereas the remaining 95.3% of the population could be discerned by the 85% cutoff.

The findings described herein show that decreased CAIX expression occurs in tumors with the highest malignant potential. This is unlikely to be explained by the loss of differentiation because there was no correlation with Fuhrman grade. Furthermore, the overall expression of CAIX appears to decrease with development of metastases; the level of CAIX is less in the metastatic lesion than in the parental primary tumor (FIG. 5). This suggests that CAIX may play a functional role in tumor progression. It is hypothesized that in the earlier stages of tumor progression, noxious conditions such as hypoxia or ischemia induce CAIX expression as an adaptation to confer proliferation advantage for tumor growth and spread; however, when this malignant potential is attained in the later stages of tumor growth, continued CAIX expression is no longer a requirement. The analysis described herein does not preclude the alternative hypothesis that the cumulative effects of genetic lesions involved in cancer progression could alter the pathways of hypoxia response (Rak et al. (2002) "What do oncogenic mutations have to do with angiogenesis/vascular dependence of tumors?" *Cancer Res.* 62:1931-1934) and therefore affect CAIX expression. Additional studies will be needed to determine whether genetic changes underlie differences in CAIX expression in the primary tumors and in metastatic lesions.

Using a Cox proportional multivariate analysis with established prognostic variables, CAIX status demonstrated independent prognostic significance for metastatic RCC. Including CAIX status with prognostic factors such as T stage, grade, and ECOG PS for patients with metastatic RCC demonstrated an increase of the area under the ROC curve from 0.66 to 0.76, indicating improved prediction of survival. For patients with localized RCC, the addition of CAIX status to the regression model did not change the area under the ROC curve.

RCC belongs to a small group of tumor types that have been shown to respond to biological immune therapy. Although the responses to systemic cytokine therapy for metastatic RCC have been promising, the overall results have been inadequate perhaps because limited activity in some patients and substantial toxicity in others. Therefore, careful patient selection and stratification to various types of adjuvant immunotherapies may delineate those patients most likely to respond to treatment. Preliminary data from the cohort of patients suggested a relationship between CAIX and immunotherapy response that could have implications for clinical-trial assignment and targeted therapies. IL-2-based immunotherapy was administered to 86 patients for metastatic disease. When stratified according to CAIX status, 73 (84%) patients had high CAIX staining and 14 (16%) had low CAIX (Table 1). All complete responses to IL-2 immunotherapy (8%) included patients within the high CAIX staining group. Furthermore, overall response rate to IL-2 was greater in the group with high CAIX (27%) than in the group with low CAIX (14%). This finding could be exploited in the design of clinical trials of IL-2-based therapy and other biological response modifiers for RCC by stratifying patients based on CAIX status. Similarly, patient recruitment for targeted therapies based on monoclonal antibodies to CAIX (Divgi et al. (1998) "Phase I/II radioimmunotherapy trial with iodine-131-labeled monoclonal antibody G250 in metastatic renal cell carcinoma," *Clin. Cancer Res.* 4:2729-2739) or immunotherapy with CAIX-based RCC vaccines (Tso et al. (2001) "Induction of G250-targeted and T-cell-mediated antitumor activity against renal cell carcinoma using a chimeric fusion protein consisting of G250 and granulocyte/monocyte-colony stimulating factor," *Cancer Res.* 61:7925-7933) should also consider stratification based on CAIX staining. The analysis described herein also found a subset of patients with high-risk localized RCC and low CAIX status that behave clinically similar to patients with metastatic disease. This may indicate the presence of micrometastasis and that adjuvant immunotherapy may be of benefit for this group of patients. Overall, given that nephrectomy for known metastatic disease has been demonstrated to be helpful in prospective trials (Flanigan (2001) "Nephrectomy followed by interferon α-2b compared with interferon α-2b alone for metastatic renal-cell cancer," *N. Engl. J. Med.* 345:1655-1659), determining a patient's CAIX status by immunohistochemistry could easily be incorporated into the selection and design of treatment regimens.

CONCLUSION

In conclusion, the analysis described herein of CAIX expression in a large number of RCC demonstrates that CAIX expression is highly associated with survivorship for kidney cancer. Low CAIX expression predicts a worse outcome for patients with locally advanced RCC and is an independent predictor of poor survival in patients with metastatic RCC. CAIX status may potentially aid in the selection of patients who might benefit from IL-2 or CAIX-targeted therapies. Furthermore, patients with high-risk localized RCC and low CAIX may be potential candidates for adjuvant immunotherapy. These observations with respect to CAIX demonstrate that the integration of molecular markers with established prognostic factors will result in more accurate prognosis and will direct novel therapies to improve the survival of patients with metastatic RCC.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes.

What is claimed is:

1. A method of providing a prognosis for survival for a human subject diagnosed with metastatic renal clear cell carcinoma, comprising:
   (a) obtaining a sample of a renal tumor or of a metastatic lesion of the renal tumor of the subject;
   (b) detecting expression of a carbonic anhydrase IX (CAIX) protein of SEQ ID NO:2 in the sample by immunohistochemical staining or immunoassay using an antibody that specifically binds to the CAIX protein of SEQ ID NO:2;
   (c) quantifying the percentage of the sample that is positive for expression of the CAIX protein;
   (d) identifying the subject as having a worse prognosis for survival if ≤85% of the sample expresses the CAIX protein or identifying the subject as having a better prognosis for survival if >85% of the sample expresses the CAIX protein; and
   (e) planning a therapy for the subject according to the prognosis.

2. The method of claim 1, wherein the expression of the CAIX protein is detected using immunohistochemical staining.

3. The method of claim 1, wherein the subject has metastasized renal cell cancer and wherein >85% of the sample expresses CAIX protein, the method comprises planning adjuvant immunotherapy for the subject.

4. The method of claim 1, wherein the antibody that specifically binds to the CAIX protein of SEQ ID NO:2 is a monoclonal antibody.

5. The method of claim 1, wherein the therapy is interleukin-2 (IL-2) immunotherapy.

* * * * *

SEQUENCE LISTING

<160> NUMBER OF SEQ ID NOS: 2

<210> SEQ ID NO 1
<211> LENGTH: 1522
<212> TYPE: DNA
<213> ORGANISM: Homo sapiens
<220> FEATURE:
<221> NAME/KEY: CDS
<222> LOCATION: (13)...(1389)
<220> FEATURE:
<221> NAME/KEY: mat_peptide
<222> LOCATION: (124)...(1389)

<400> SEQUENCE: 1

```
acagtcagcc gc atg gct ccc ctg tgc ccc agc ccc tgg ctc cct ctg ttg       51
           Met Ala Pro Leu Cys Pro Ser Pro Trp Leu Pro Leu Leu
               -35                 -30                 -25 atc ccg gcc cct gct cca ggc ctc act gtg caa ctg ctg tca ctg              99
Ile Pro Ala Pro Ala Pro Gly Leu Thr Val Gln Leu Leu Ser Leu
            -20                 -15                 -10 ctg ctt ctg atg cct gtc cat ccc cag agg ttg ccc cgg atg cag gag         147
Leu Leu Leu Met Pro Val His Pro Gln Arg Leu Pro Arg Met Gln Glu
         -5                  -1   1                   5 gat tcc ccc ttg gga gga ggc tct tct ggg gaa gat gac cca ctg ggc         195
Asp Ser Pro Leu Gly Gly Gly Ser Ser Gly Glu Asp Asp Pro Leu Gly
     10                  15                  20 gag gag gat ctg ccc agt gaa gag gat tca ccc aga gag gag gat cca         243
Glu Glu Asp Leu Pro Ser Glu Glu Asp Ser Pro Arg Glu Glu Asp Pro
 25                 30                  35                  40 ccc gga gag gag gat cta cct gga gag gag gat cta cct gga gag gag         291
Pro Gly Glu Glu Asp Leu Pro Gly Glu Glu Asp Leu Pro Gly Glu Glu
                 45                  50                  55 gat cta cct gaa gtt aag cct aaa tca gaa gaa gag ggc tcc ctg aag         339
Asp Leu Pro Glu Val Lys Pro Lys Ser Glu Glu Glu Gly Ser Leu Lys
             60                  65                  70 tta gag gat cta cct act gtt gag gct cct gga gat cct caa gaa ccc         387
Leu Glu Asp Leu Pro Thr Val Glu Ala Pro Gly Asp Pro Gln Glu Pro
         75                  80                  85 cag aat aat gcc cac agg gac aaa gaa ggg gat gac cag agt cat tgg         435
Gln Asn Asn Ala His Arg Asp Lys Glu Gly Asp Asp Gln Ser His Trp
     90                  95                  100 cgc tat gga ggc gac ccg ccc tgg ccc cgg gtg tcc cca gcc tgc gcg         483
Arg Tyr Gly Gly Asp Pro Pro Trp Pro Arg Val Ser Pro Ala Cys Ala
105                 110                 115                 120 ggc cgc ttc cag tcc ccg gtg gat atc cgc ccc cag ctc gcc gcc ttc         531
Gly Arg Phe Gln Ser Pro Val Asp Ile Arg Pro Gln Leu Ala Ala Phe
                125                 130                 135 tgc ccg gcc ctg cgc ccc ctg gaa ctc ctg ggc ttc cag ctc ccg ccg         579
Cys Pro Ala Leu Arg Pro Leu Glu Leu Leu Gly Phe Gln Leu Pro Pro
            140                 145                 150 ctc cca gaa ctg cgc ctg cgc aac aat ggc cac agt gtg caa ctg acc         627
Leu Pro Glu Leu Arg Leu Arg Asn Asn Gly His Ser Val Gln Leu Thr
        155                 160                 165 ctg cct cct ggg cta gag atg gct ctg ggt ccc ggg cgg gag tac cgg         675
Leu Pro Pro Gly Leu Glu Met Ala Leu Gly Pro Gly Arg Glu Tyr Arg
    170                 175                 180 gct ctg cag ctg cat ctg cac tgg ggg gct gca ggt cgt ccg ggc tcg         723
Ala Leu Gln Leu His Leu His Trp Gly Ala Ala Gly Arg Pro Gly Ser
185                 190                 195                 200 gag cac act gtg gaa ggc cac cgt ttc cct gcc gag atc cac gtg gtt         771
Glu His Thr Val Glu Gly His Arg Phe Pro Ala Glu Ile His Val Val
                205                 210                 215
```

-continued

```
cac ctc agc acc gcc ttt gcc aga gtt gac gag gcc ttg ggg cgc ccg      819
His Leu Ser Thr Ala Phe Ala Arg Val Asp Glu Ala Leu Gly Arg Pro
        220                 225                 230 gga ggc ctg gcc gtg ttg gcc gcc ttt ctg gag gag ggc ccg gaa gaa      867
Gly Gly Leu Ala Val Leu Ala Ala Phe Leu Glu Glu Gly Pro Glu Glu
        235                 240                 245 aac agt gcc tat gag cag ttg ctg tct cgc ttg gaa gaa atc gct gag      915
Asn Ser Ala Tyr Glu Gln Leu Leu Ser Arg Leu Glu Glu Ile Ala Glu
    250                 255                 260 gaa ggc tca gag act cag gtc cca gga ctg gac ata tct gca ctc ctg      963
Glu Gly Ser Glu Thr Gln Val Pro Gly Leu Asp Ile Ser Ala Leu Leu
265                 270                 275                 280 ccc tct gac ttc agc cgc tac ttc caa tat gag ggg tct ctg act aca     1011
Pro Ser Asp Phe Ser Arg Tyr Phe Gln Tyr Glu Gly Ser Leu Thr Thr
                285                 290                 295 ccg ccc tgt gcc cag ggt gtc atc tgg act gtg ttt aac cag aca gtg     1059
Pro Pro Cys Ala Gln Gly Val Ile Trp Thr Val Phe Asn Gln Thr Val
            300                 305                 310 atg ctg agt gct aag cag ctc cac acc ctc tct gac acc ctg tgg gga     1107
Met Leu Ser Ala Lys Gln Leu His Thr Leu Ser Asp Thr Leu Trp Gly
        315                 320                 325 cct ggt gac tct cgg cta cag ctg aac ttc cga gcg acg cag cct ttg     1155
Pro Gly Asp Ser Arg Leu Gln Leu Asn Phe Arg Ala Thr Gln Pro Leu
    330                 335                 340 aat ggg cga gtg att gag gcc tcc ttc cct gct gga gtg gac agc agt     1203
Asn Gly Arg Val Ile Glu Ala Ser Phe Pro Ala Gly Val Asp Ser Ser
345                 350                 355                 360 cct cgg gct gct gag cca gtc cag ctg aat tcc tgc ctg gct gct ggt     1251
Pro Arg Ala Ala Glu Pro Val Gln Leu Asn Ser Cys Leu Ala Ala Gly
                365                 370                 375 gac atc cta gcc ctg gtt ttt ggc ctc ctt ttt gct gtc acc agc gtc     1299
Asp Ile Leu Ala Leu Val Phe Gly Leu Leu Phe Ala Val Thr Ser Val
            380                 385                 390 gcg ttc ctt gtg cag atg aga agg cag cac aga agg gga acc aaa ggg     1347
Ala Phe Leu Val Gln Met Arg Arg Gln His Arg Arg Gly Thr Lys Gly
        395                 400                 405 ggt gtg agc tac cgc cca gca gag gta gcc gag act gga gcc               1389
Gly Val Ser Tyr Arg Pro Ala Glu Val Ala Glu Thr Gly Ala
    410                 415                 420 tagaggctgg atcttggaga atgtgagaag ccagccagag gcatctgagg gggagccggt    1449
aactgtcctg tcctgctcat tatgccactt ccttttaact gccaagaaat tttttaaaat    1509
aaatatttat aat                                                        1522

<210> SEQ ID NO 2
<211> LENGTH: 459
<212> TYPE: PRT
<213> ORGANISM: Homo sapiens
<220> FEATURE:
<221> NAME/KEY: mat_peptide
<222> LOCATION: (124)...(1389)

<400> SEQUENCE: 2

Met Ala Pro Leu Cys Pro Ser Pro Trp Leu Pro Leu Leu Ile Pro Ala
        -35                 -30                 -25

Pro Ala Pro Gly Leu Thr Val Gln Leu Leu Leu Ser Leu Leu Leu Leu
    -20                 -15                 -10

Met Pro Val His Pro Gln Arg Leu Pro Arg Met Gln Glu Asp Ser Pro
-5                  -1   1                   5                  10
```

```
Leu Gly Gly Gly Ser Ser Gly Glu Asp Asp Pro Leu Gly Glu Asp
            15                  20                  25
Leu Pro Ser Glu Glu Asp Ser Pro Arg Glu Glu Asp Pro Pro Gly Glu
        30                  35                  40
Glu Asp Leu Pro Gly Glu Glu Asp Leu Pro Gly Glu Glu Asp Leu Pro
    45                  50                  55
Glu Val Lys Pro Lys Ser Glu Glu Gly Ser Leu Lys Leu Glu Asp
60                  65                  70                  75
Leu Pro Thr Val Glu Ala Pro Gly Asp Pro Gln Glu Pro Gln Asn Asn
                80                  85                  90
Ala His Arg Asp Lys Glu Gly Asp Asp Gln Ser His Trp Arg Tyr Gly
            95                  100                 105
Gly Asp Pro Pro Trp Pro Arg Val Ser Pro Ala Cys Ala Gly Arg Phe
        110                 115                 120
Gln Ser Pro Val Asp Ile Arg Pro Gln Leu Ala Ala Phe Cys Pro Ala
    125                 130                 135
Leu Arg Pro Leu Glu Leu Leu Gly Phe Gln Leu Pro Pro Leu Pro Glu
140                 145                 150                 155
Leu Arg Leu Arg Asn Asn Gly His Ser Val Gln Leu Thr Leu Pro Pro
                160                 165                 170
Gly Leu Glu Met Ala Leu Gly Pro Gly Arg Glu Tyr Arg Ala Leu Gln
            175                 180                 185
Leu His Leu His Trp Gly Ala Ala Gly Arg Pro Gly Ser Glu His Thr
        190                 195                 200
Val Glu Gly His Arg Phe Pro Ala Glu Ile His Val Val His Leu Ser
    205                 210                 215
Thr Ala Phe Ala Arg Val Asp Glu Ala Leu Gly Arg Pro Gly Gly Leu
220                 225                 230                 235
Ala Val Leu Ala Ala Phe Leu Glu Glu Gly Pro Glu Glu Asn Ser Ala
                240                 245                 250
Tyr Glu Gln Leu Leu Ser Arg Leu Glu Glu Ile Ala Glu Glu Gly Ser
            255                 260                 265
Glu Thr Gln Val Pro Gly Leu Asp Ile Ser Ala Leu Leu Pro Ser Asp
        270                 275                 280
Phe Ser Arg Tyr Phe Gln Tyr Glu Gly Ser Leu Thr Thr Pro Pro Cys
    285                 290                 295
Ala Gln Gly Val Ile Trp Thr Val Phe Asn Gln Thr Val Met Leu Ser
300                 305                 310                 315
Ala Lys Gln Leu His Thr Leu Ser Asp Thr Leu Trp Gly Pro Gly Asp
                320                 325                 330
Ser Arg Leu Gln Leu Asn Phe Arg Ala Thr Gln Pro Leu Asn Gly Arg
            335                 340                 345
Val Ile Glu Ala Ser Phe Pro Ala Gly Val Asp Ser Ser Pro Arg Ala
        350                 355                 360
Ala Glu Pro Val Gln Leu Asn Ser Cys Leu Ala Ala Gly Asp Ile Leu
    365                 370                 375
Ala Leu Val Phe Gly Leu Leu Phe Ala Val Thr Ser Val Ala Phe Leu
380                 385                 390                 395
Val Gln Met Arg Arg Gln His Arg Arg Gly Thr Lys Gly Gly Val Ser
                400                 405                 410
Tyr Arg Pro Ala Glu Val Ala Glu Thr Gly Ala
            415                 420
```